United States Patent [19]

Posin et al.

[11] Patent Number: 4,753,654
[45] Date of Patent: * Jun. 28, 1988

[54] ULTRAVIOLET RADIATION ABSORBING INTRAOCULAR LENS

[75] Inventors: Thomas Posin, Walnut; Daniel D. Lawson, Arcadia, both of Calif.

[73] Assignee: Optical Radiation Corporation, Azusa, Calif.

[*] Notice: The portion of the term of this patent subsequent to Jan. 13, 2004 has been disclaimed.

[21] Appl. No.: 948,328

[22] Filed: Dec. 31, 1986

Related U.S. Application Data

[63] Continuation of Ser. No. 713,014, Mar. 18, 1985, Pat. No. 4,636,212, which is a continuation-in-part of Ser. No. 376,666, May 10, 1982, abandoned.

[51] Int. Cl.⁴ ............................................. A61F 2/16
[52] U.S. Cl. ........................................ 623/6; 623/66; 523/137; 526/75; 351/162; 351/163; 264/1.1
[58] Field of Search ............... 623/6, 66 C; 351/162, 351/163, 177; 523/137; 526/75, 313; 106/288 Q; 264/1.1

[56] References Cited

U.S. PATENT DOCUMENTS

| 2,518,099 | 8/1950 | Tillyer . | |
| 3,162,676 | 12/1964 | Goldberg et al. | 523/137 |
| 3,173,893 | 3/1965 | Fertig et al. | 523/137 |
| 3,263,005 | 7/1966 | Emerick . | |
| 3,852,032 | 12/1974 | Urbach | 351/163 X |
| 3,996,627 | 12/1976 | Deeg | 623/6 |
| 4,304,895 | 12/1981 | Loshaek | 526/313 |
| 4,310,650 | 1/1982 | Gupta et al. | 526/313 |
| 4,390,676 | 6/1983 | Loshaek | 526/313 |
| 4,636,212 | 1/1987 | Posin et al. | 623/6 |

FOREIGN PATENT DOCUMENTS

| 1031200 | 5/1978 | Canada . |
| 885986 | 1/1962 | United Kingdom . |
| 1480492 | 7/1977 | United Kingdom . |

OTHER PUBLICATIONS

National Starch and Chemical Corporation, Technical Services Bulletin titled Permasorb MA (pp. 1-2).
J. Fertig, A. I. Goldberg, & M. Skoultchi, *Ultraviolet Stabilizing Monomers and Polymers. II. Synthesis and Polymerization of Acrylate & Methacrylate Derivatives of 2,4-Dihydroxybenzophenone*, Journal of Applied Polymer Science, vol. 10, pp. 663-672 (1966).
Amitava Gupta, Andre Yavrouian, & Salvadore Di Stefano, Charles D. Merritt & Gary W. Scott, *Photophysical and Photochemical Properties of Poly(2-Hydoxy-3-Allyl-4,4'Dimethoxybenzophenone-co-Methyl Methacrylate): Photochemical Processes in Polymeric Systems, 3*, Macromolecules, vol. 13, p. 821 (Jul.-Aug. 1980).
Rohm and Haas Company, Technical Data entitled *Plexiglas Injection and Extrusion Molding Powders* (Dec. 1968), pp. 1-10 & 12-19.
*Synthetic Resins*, Gotoda, Chemical Abstract, vol. 88, 1978, p. 41 88:192085E.
The Food and Drug Administration, *The Law of Flexible Hydrophilic Contact Lenses*, Journal of the American Optometric Assoc., vol. 43, No. 3, Mar. 1973.
M. Mainster, *Spectral Transmittance of Intraocular Lenses and Retinal Damage from Intense Light Sources*, American Journal of Ophthmology 85:167170 (1978).

Primary Examiner—Ronald L. Frinks
Attorney, Agent, or Firm—Christie, Parker & Hale

[57] ABSTRACT

An intraocular lens capable of absorbing ultraviolet radiation and, additionally, a method for forming the lens is provided. The intraocular lens comprises a polymer matrix that is biocompatible with body tissue and fluids and comprises polymethylmethacrylate and a chromophoric compound. The intraocular lens preferably has about the same capability for absorbing ultraviolet radiation as does the natural crystalline lens of the eye. In one embodiment, the intraocular lens is formed by co-polymerizing a polymerizable derivate of 2,4-dihydroxybenzophenone and methyl methacrylate monomer to form an ultraviolet light absorbing co-polymer additive. The co-polymer additive is mixed with methyl methacrylate monomer for forming a prepolymer solution that is then cured. The intraocular lens is formed from the solid cured co-polymer.

10 Claims, 1 Drawing Sheet

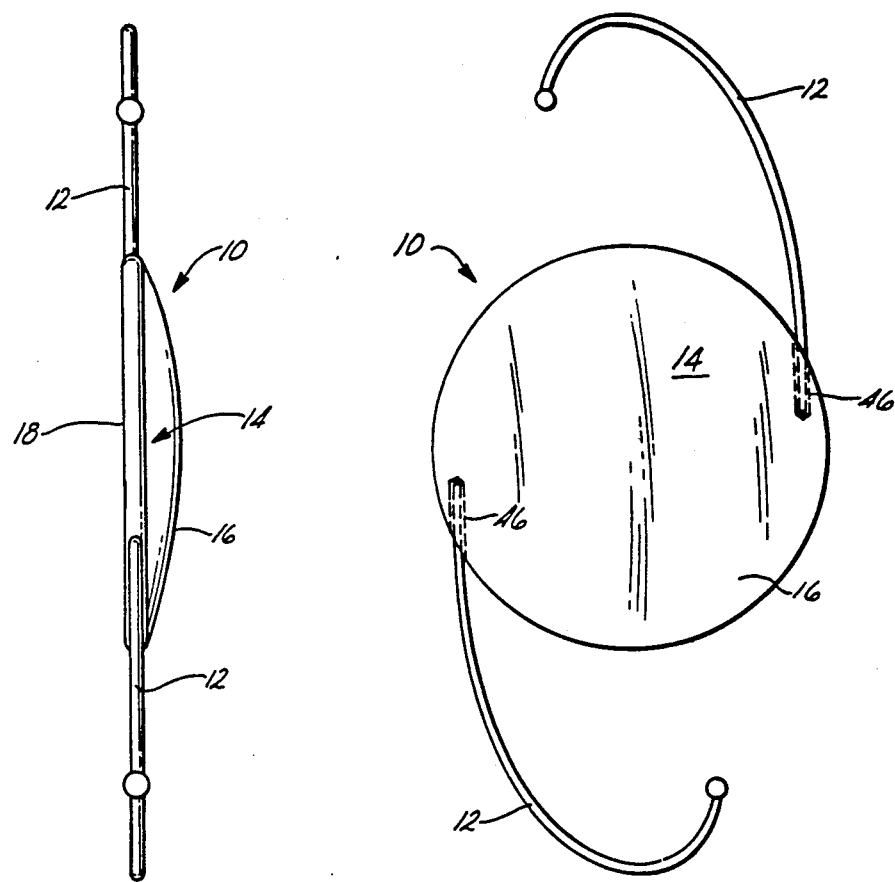

ULTRAVIOLET RADIATION ABSORBING INTRAOCULAR LENS

CROSS-REFERENCE TO RELATED APPLICATIONS

This application is a continuation of application Ser. No. 713,014 filed Mar. 18, 1985, now U.S. Pat. No. 4,636,212, which was a continuation-in-part of application Ser. No. 376,666 filed May 10, 1982, abandoned. Application Ser. No. 376,666 is incorporated herein by this reference.

FIELD OF THE INVENTION

This invention relates to an intraocular lens capable of absorbing ultraviolet radiation and, additionally, to a method for forming the lens.

BACKGROUND OF THE INVENTION

The problem of restoring useful vision to a human eye after its cataractus natural lens has been removed has been with us since the introduction of cataract surgery. The solution to this problem has included the use of spectacle lenses, contact lenses, and permanent implantation into the eye of a man-made lens, i.e., an intraocular lens.

Since 1949, when the first implant of an intraocular lens was made, hundreds of thousands of persons have had such implants. Recent advances in cataract surgery have now made the intraocular lens implant procedure a safer and more popular alternative. For example, it is estimated that nearly 40 percent of the people now undergoing cataract surgery select a lens implant, i.e., an intraocular lens, instead of wearing contact lenses or thick cataract-type spectacles.

Although silicate glass was initially considered for use in intraocular lenses, generally such lenses are now made of polymethylmethacrylate (PMMA). PMMA is a polymer formed by polymerization of methyl methacrylate monomer (MMA monomer).

In the aphakic eye, the cornea and crystalline lens work together to absorb ultraviolet radiation or light. The cornea absorbs virtually all of the ultraviolet radiation below 300 nanometers (nm) that reaches the eye (almost all ultraviolet radiation below 286 nm is absorbed by the ozone layer in the earth's atmosphere). Although the cornea also absorbs a portion of the ultraviolet radiation between 300 nm and 400 nm, the natural crystalline lens absorbs the major portion of the ultraviolet radiation in this range.

Thus, when the natural crystalline lens is removed from the eye, ultraviolet radiation that would otherwise have been absorbed by the natural lens can reach the retina.

Recent evidence indicates that the retina can be damaged by ultraviolet radiation. For example, ultraviolet radiation is considered by many opthamologists as a casual factor in erythropsia ("pink vision"), cystoid macular edema, and macular degeneration.

It is thought that retinal damage by ultraviolet radiation results from absorption of light energy and conversion of this energy into heat within the cells. Damage to the retina can also result from molecular absorption of ultraviolet radiation which can place a cellular molecular species in an excited state, resulting in various chemical reactions of the excited species.

It appears that damage to the eye from ultraviolet radiation is cumulative. Thus, it is very important that an individual who has his natural crystalline lens removed take precautions to shield the retina of his eye from ultraviolet radiation.

Studies have also provided supporting evidence to show that ultraviolet radiation is a causal factor in polymer degradation of polymethylmethacrylate, the material from which intraocular lenses can be made. Thus, it is also important that an implanted intraocular lens be protected from ultraviolet radiation.

Since polymethylmethacrylate does not absorb any significant portion of the ultraviolet radiation in the 300–400 nm range, persons who have had a polymethylmethacrylate intraocular lens implant have been prone to retinal damage from ultraviolet radiation or have had to protect their pseudophakic eye by using spectacle lenses having ultraviolet light absorbing capability.

It is important, therefore, that an intraocular lens be provided that has ultraviolet absorbing capabilities, firstly to protect the retina of the eye from radiation damage, and secondly to retard damage to the intraocular lens itself from such ultraviolet radiation. It is desired that the ultraviolet absorbing intraocular lens have absorbing capabilities which approximate the capabilities of the natural crystalline lens which has been removed. Further, the ultraviolet absorbing intraocular lens must be biocompatible with body fluids and tissue and have desired optical properties.

SUMMARY OF THE INVENTION

This invention relates to an ultraviolet radiation absorbing intraocular lens for implantation into a human eye. The intraocular lens comprises an ultraviolet radiation absorbing co-polymer physically trapped within a polymer matrix, such as polymethylmethacrylate for example. The ultraviolet absorbing co-polymer is formed by co-polymerizing a polymerizable derivative of dihydroxybenzophenone with a monomer suitable for making intraocular lenses, e.g., methyl methacrylate. The intraocular lens is biocompatible with body tissue and fluids and has about the same capability for absorbing ultraviolet radiation as does the natural crystalline lens of the eye.

In an exemplary embodiment, the ultraviolet radiation absorbing intraocular lens is formed by co-polymerizing a polymerizable derivative of 2,4-dihydroxybenzophenone and methyl methacrylate monomer to form an ultraviolet radiation absorbing co-polymer additive. The ultraviolet radiation absorbing co-polymer additive is mixed with methyl methacrylate monomer for forming a prepolymer solution. The prepolymer solution is cured to form the ultraviolet radiation absorbing intraocular lens.

BRIEF DESCRIPTION OF THE DRAWINGS

These and other features, aspects, and advantages of the present invention will become more apparent when considered with respect to the following description, appended claims, and accompanying drawings, wherein:

FIG. 1 is a plan view of an exemplary intraocular lens assembly comprising a lens having an ultraviolet radiation absorbing capability provided in accordance with practice of this invention; and FIG. 2 is a side view of the exemplary intraocular lens assembly of FIG. 1.

DETAILED DESCRIPTION

Referring to FIGS. 1 and 2, there is shown a plan view (FIG. 1) and a side view (FIG. 2) of an intraocular lens assembly 10 for implantation into the human eye provided in accordance with practice of principles of this invention. The intraocular lens assembly 10 comprises one or more non-optical "haptic" components 12 connected to an optical component or lens 14. The haptic components are useful for supporting or attaching the lens to an aphakic eye.

The lens 14 comprises an ultraviolet radiation absorbing co-polymer physically trapped within a polymer matrix for example, of polymethylmethacrylate. The ultraviolet radiation absorbing co-polymer is formed by co-polymerizing a polymerizable chromophoric compound for example, a polymerizable derivative of dihydroxybenzophenone, with a monomer suitable for making such lenses, for example, with methyl methacrylate. The resulting intraocular lens preferably has about the same capability for absorbing ultraviolet radiation as does the natural crystalline lens of the eye and is biocompatible with body tissue and fluids.

Although the lens 14 of the assembly 10 is a "plano-convex lens", i.e., it has a convex surface 16 on one side and a flat or planar surface 18 on its other side, lenses having any desired design configuration can be provided. Further, although two haptics 12 are shown, fewer or more haptics can be used as desired and the haptics can have configurations other than the configuration of the haptics shown in the exemplary embodiment.

The lens 14 preferably is formed in a series of steps which include co-polymerizing the selected polymerizable chromophoric compound with methyl methacrylate monomer to form an ultraviolet radiation absorbing co-polymer additive; dissolving the ultraviolet radiation absorbing co-polymer additive in methyl methacrylate monomer to form a prepolymer solution; curing the prepolymer solution; and finishing the lens as necessary from the cured prepolymer.

Exemplary chromophoric compounds useful in practice of this invention are ethylenically unsaturated derivatives of dihydroxybenzophenone selected from the group consisting of:

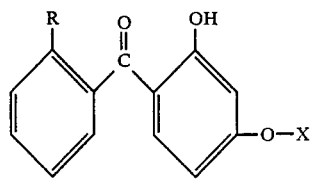

and

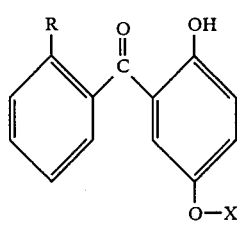

and

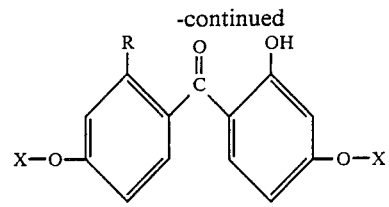

and

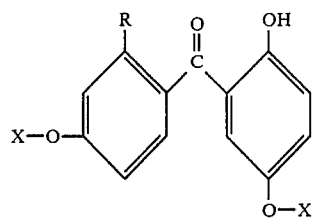

and

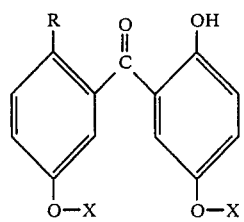

wherein X is an ethylenically unsaturated radical selected from the group consisting of acryloxy beta-hydroxypropyl and methacryloxy beta-hydroxypropyl radicals and wherein R represents a radical selected from the class consisting of hydrogen and hydroxy radicals.

As representative of dihydroxybenzophenone derivatives useful in practice of this invention, there may include derivatives of 2,4-dihydroxybenzophenone such as 4-acryloxy beta-hydroxypropyl ether of 2,4-dihydroxybenzophenone; the 4-methacryloxy beta-hydroxypropyl ether of 2,4-dihydroxybenzophenone, i.e., 2-hydroxy-4-(2-hydroxy-3-methacrylyloxy)propoxybenzophenone; the 4-acryloxy beta-hydroxypropyl ether of 2,2′,4-trihydroxybenzophenone; the 4-methacryloxy beta-hydroxypropyl ether of 2,2′,4-trihydroxybenzophenone; the 4,4′-di(acryloxy beta-hydroxypropyl) ether of 2,2′,4,4′-tetrahydroxybenzophenone; and the 4,4′-di(methacryloxy beta-hydroxypropyl) ether of 2,2′,4,4′-tetrahydroxybenzophenone. Thus, mono- and difunctional ethylenically unsaturated derivatives of dihydroxybenzophenone are useful in practice of the invention.

Other chromophoric compounds may also be used such as allylic substituted benzophenones, i.e., 2-hydroxy-3-allyl-4-4′ dimethoxybenzophenone, ethylenically or allylically substituted phenyl benzotriazoles, provided that they are capable of readily undergoing vinyl-type polymerization reactions and thus can form a co-polymer with methyl methacrylate monomer.

Preferably, the chromophoric compound is a material sold by National Starch and Chemical Corporation, Resin Division, Bridgewater, N.J., under the trademark PERMASORB MA. PERMASORB MA is represented by National Starch to include 2-hydroxy-4-(2-hydroxy-3-methacrylyloxy) propoxybenzophenone, which has the following chemical structure:

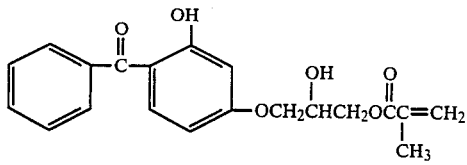

Additional information relating to chromophoric compounds useful in practice of this invention can be found in U.S. Pat. No. 3,162,676 issued on Dec. 22, 1964, to Goldberg et al. U.S. Pat. No. 3,162,676 is incorporated herein by this reference.

In a presently preferred process for forming an ultraviolet radiation absorbing lens, methyl methacrylate monomer and PERMASORB MA are dissolved in dry ethyl acetate to form a "monomer mix". An "initiator mix" is prepared by dissolving an initiator in dry ethyl acetate. Presently preferred initiators are benzoyl peroxide, tert-butyl hydro peroxide, cumene hydro peroxide, 2-azobisisobutyronitrile, and azoisobutylnitrile (AIBN) and the like.

The monomer mix and initiator mix are mixed together in a reaction flask and heated to reflux at about 77° C.±3° C. for a period of time to form the co-polymer of methylmethacrylate/2-hydroxy-4-PERMASORB MA (PMMA/PERMASORB MA co-polymer). The reaction mixture is then cooled and added to 5 to 6 times its volume of anhydrous methanol which causes the ultraviolet radiation absorbing PMMA/PERMASORB MA co-polymer to precipitate as a solid polymer mass. The ultraviolet radiation absorbing solid polymer mass is comminuted, i.e., ground into a fine powder, and dried. The comminuted co-polymer is purified by "Soxhlet" extraction to remove remaining unreacted raw materials and solvents. The solid co-polymer is then vacuum dried and comminuted. The comminuted co-polymer (the ultraviolet radiation absorbing PMMA/PERMASORB MA co-polymer additive) is dissolved in methyl methacrylate monomer to form a prepolymer solution and the prepolymer solution is cured to form the ultraviolet radiation absorbing intraocular lens of this invention wherein the PMMA/PERMASORB MA co-polymer is trapped within the polymethylmethacrylate matrix of the lens.

Standard methods known in the art for curing prepolymers can be used to form the intraocular lens of this invention. For example, the prepolymer solution can be poured into a mold having a desired optical configuration. The mold, after it is filled, is then placed into an autoclave and subjected to elevated temperature and pressure conditions for curing the lens. After completion of the desired time-temperature/pressure cycle in the autoclave, the mold is removed therefrom and the lens blank is removed from the mold. The edges are then removed from the lens blank by machining and haptics are connected to the lens in appropriate holes formed in its edges. After the haptics are attached, the finished intraocular lens is inspected, sterilized, and packaged for shipment.

Preferably, the ratio of the weight of the chromophoric compound to the total weight of chromophoric compound plus methyl methacrylate monomer in the monomer mix is small enough so that the co-polymer formed, i.e., the co-polymer additive, is soluble in polymethylmethacrylate. This is important so that the finished intraocular lens has a desired optical clarity. For example, it is preferred that the ratio of the weight of PERMASORB MA to the total weight of PERMASORB MA plus methyl methacrylate monomer in the monomer mix is such that, upon polymerization of the monomer mix, less than about 15 percent by weight of the PMMA/PERMASORB MA co-polymer additive formed comprises PERMASORB MA. It is important that the PMMA/PERMASORB MA co-polymer comprises less than about 15% by weight PERMASORB MA because it has been found that when such a co-polymer additive comprises a higher weight percentage of PERMASORB MA, the co-polymer is not soluble at any proportion in polymethylmethacrylate. Thus, lenses formed using PMMA/PERMASORB MA co-polymer additive comprising more than about 15% by weight PERMASORB MA tend to be cloudy or hazy. For example, lenses formed using PMMA/PERMASORB MA co-polymer additives comprising 16.1%, 22.5%, and 50% by weight PERMASORB MA all produced hazy lenses, while lenses formed of PMMA/PERMASORB MA co-polymer additive comprising 5.7%, 10%, and 12% were clear. Surprisingly, this appears to be the case regardless of the weight ratio of PMMA/PERMASORB MA co-polymer additive to MMA monomer used to form the PMMA/PERMASORB MA intraocular lens.

Preferably, the finished lens comprises from about four percent to about five percent by weight PERMASORB MA.

It has been found that when PERMASORB MA and methyl methacrylate monomer are co-polymerized under reaction conditions such as those described in detail below, only about 50 to 60 percent by weight of the PERMASORB MA in the monomer mixture is incorporated into the co-polymer additive formed. This must be taken into account when selecting the desired ratio of the weight of PERMASORB MA to the weight of methyl methacrylate monomer used for forming the monomer mixture to provide a co-polymer additive having a desired, selected weight percent of PERMASORB MA.

The following non-limiting example of a presently preferred process for forming an ultraviolet radiation absorbing intraocular lens material comprising an ultraviolet absorbing co-polymer, consisting essentially of methyl methacrylate monomer co-polymerized with PERMASORB MA, physically trapped within a polymethylmethacrylate polymer matrix is presented to further demonstrate practice of principles of this invention.

EXAMPLE 1

PREPARATION OF AN ULTRAVIOLET RADIATION ABSORBING INTRAOCULAR LENS MATERIAL 80 grams of methyl methacrylate monomer supplied by Rohm & Haas Company and 20 grams of PERMASORB MA were dissolved at room temperature in 20 grams of dry ethyl acetate to form a monomer mix.

Separately, an initiator mix was prepared by dissolving 1 gram of azoisobutylnitrile (AIBN) at room temperature in 25 grams of dry ethyl acetate.

20 grams of the monomer mix, 30 grams of ethyl acetate, and 0.5 grams of AIBN were charged into a reaction flask equipped with a stirring motor and heating mantle. The charge in the reaction flask was brought to reflux (77° C.) and held at reflux for 15 minutes. Nitrogen was bubbled through the charge in the reaction flask during the reaction and it was constantly stirred.

After the 15-minute time period, dropwise additions of the balance of the monomer mix (100 grams) and initiator mix (26 grams) were started simultaneously into the refluxing materials in the reaction flask. (Stirring and nitrogen bubbling was continued during the entire reaction.) The monomer mix was added over a period of about 2½ hours, while the initiator mix was added over a period of about 3½ hours. Following the completion of the monomer mix addition, 30 grams of dry ethyl acetate were added in dropwise fashion to the reaction flask over a period of 30 minutes.

Following the completion of all additions, reflux was continued for 1½ hours. At the end of the 1½ hour period, 60 grams of ethyl acetate were added and the reaction mixture was cooled to room temperature. Methanol, at about 5 to 6 times the volume of the cooled reaction mixture, was then added slowly (about 5 to 10 minutes) to the reaction mixture (while stirring) to precipitate PMMA/PERMASORB MA co-polymer that had formed. The resultant wet PMMA/PERMASORB MA co-polymer blob was placed in a blender with 200 ml of methanol at room temperature to form a fine suspension of the co-polymer. The co-polymer was then filtered and extracted in methanol with a Soxhlet extractor using a cellulose thimble. After methanol extraction, the co-polymer blob was placed in a blender with methanol and again a fine suspension of the co-polymer was formed. The suspension was filtered and, to remove any cellulose fibers from the co-polymer, the filtered co-polymer blob was placed in methylene chloride ($CH_2Cl_2$) and dissolved. The methylene chloride/co-polymer solution was then filtered and the co-polymer was reprecipitated from the filtered solution in methanol. The co-polymer (the PMMA/PERMASORB MA co-polymer additive) was then dried and ground into a fine powder.

To form the prepolymer solution, about 30 percent by weight of the co-polymer powder (the PMMA/PERMASORB MA co-polymer additive) was placed into a reaction flask with about 70 percent by weight methyl methacrylate monomer. The monomer/co-polymer mixture was stirred for about 14 hours at room temperature to dissolve the powder. Benzoyl peroxide initiator was added (0.05% by weight based on the weight of methyl methacrylate monomer) and mixed into the prepolymer solution for about 30 minutes at room temperature. The prepolymer solution was then subjected to a vacuum process to remove any dissolved gases and air bubbles.

The degassed prepolymer solution was filtered through a 5 micron filter as it was being poured into a mold for curing. The mold was placed into a casting chamber and subjected to conditions of temperature, pressure, and time for polymerizing or curing the prepolymer solution to form a solid polymeric ultraviolet radiation absorbing material comprising the ultraviolet radiation absorbing co-polymer additive physically trapped within a polymethylmethacrylate polymer matrix.

An intraocular lens provided in accordance with this invention is finished from the ultraviolet radiation absorbing polymeric material by machining and other appropriate lens finishing operations.

It is necessary that a device that is to be implanted in the body, such as an intraocular lens provided in accordance with practice of principles of this invention, is biocompatible with body tissue and fluids, i.e., it does not produce adverse local or systemic responses or cause sensitization leading to an allergic response when implanted. To determine biocompatibility of ultraviolet absorbing materials prepared in accordance with Example 1, such materials were tested first to determine whether raw materials used in their preparation tend to leach from them, thereby possibly inhibiting biocompatibility. Further testing of the ultraviolet radiation absorbing materials prepared in accordance with Example 1 is, however, required by the Food and Drug Administration (FDA) to insure that they are biocompatible with body tissues and fluids and can be used in devices that are to be implanted in the human body. Therefore, such materials were tested directly for biocompatibility by various accepted biological tests.

The details of the tests and the results are set forth in Examples 2 to 20 below.

EXAMPLE 2

MMA MONOMER LEACHING BY MEASUREMENT OF RESIDUAL MONOMER IN MATERIALS PREPARED IN ACCORDANCE WITH EXAMPLE 1

The amount of MMA monomer that leaches from materials prepared in accordance with Example 1 (test material) was determined by measuring the amount of MMA monomer in such a material before and after a 24-hour saline extraction.

Three cast sheets of test material were subjected to ethylene oxide sterilization. The three sample sheets were then divided into two parts each and labeled as follows: UVI-EXPOSED, UVI-UNEXPOSED, UVII-EXPOSED, UVII-UNEXPOSED, UVIII-EXPOSED, and UVIII-UNEXPOSED.

All samples labeled as UV exposed were then exposed for 235 hours to UV radiation using an SP-5000 HG-XE UV Exposure System manufactured by Optical Radiation Corporation, assignee of this application. This is equivalent to 14.5 years of normal UV radiation exposure.

Each of the six labeled sample parts were then divided into smaller pieces (for subsequent sampling). A representative piece of each sample part was removed for % MMA residual monomer analysis. % MMA monomer was measured by dissolving the entire piece of material in acetone and performing a gas chromatograph (GC) analysis for MMA monomer content. The method used to perform the GC analysis was similar to Galin, M. A. et al; Methyl Methacrylate Monomer in Intraocular Lenses of PMMA; Arch. Opthalmol, Vol. 98, January 1980, pp 120-121. All other sample pieces were placed into separate glass containers filled with USP saline solution for extraction at 37±4° C. After 24 hours of extraction, a test material sample was removed from each container and analyzed for % MMA residual monomer. Again, % MMA monomer was measured by dissolving the entire piece of test material in acetone and performing GC analysis for MMA content. The results are listed in Table 1.

TABLE 1

| Sample | Results % MMA Residual Monomer | |
|---|---|---|
|  | 0 Hours | 24 Hours |
| UVI-UNEXPOSED | 0.61 | 0.55 |
| UVI-EXPOSED | 0.56 | 0.57 |
| UVII-UNEXPOSED | 0.62 | 0.53 |

TABLE 1-continued

Results
% MMA Residual Monomer

| Sample | 0 Hours | 24 Hours |
|---|---|---|
| UVII-EXPOSED | 0.53 | 0.49 |
| UVIII-UNEXPOSED | 0.53 | 0.58 |
| UVIII-EXPOSED | 0.56 | 0.53 |

The results for both irradiation exposed and non-exposed test materials indicate that MMA monomer does not leach from such materials.

EXAMPLE 3

MMA MONOMER LEACHING BY MEASUREMENT OF MONOMER IN EXTRACT

The amount of MMA monomer that leaches from materials prepared in accordance with Example 1 (test material) was determined by measuring the amount of MMA monomer in saline extract during a 21-day saline extraction.

Three cast sheets of test material were subjected to ethylene oxide sterilization. The three sample sheets of test material were then divided into two parts each and labeled as follows: UVIA-EXPOSED, UVIA-UNEXPOSED, UVIIA-EXPOSED, UVIIA-UNEXPOSED, UVIIIA-EXPOSED, and UVIIIA-UNEXPOSED.

All test material samples labeled as UV exposed were then exposed for 127 hours to UV radiation using an SP-5000 HG-XE UV Exposure System manufactured by Optical Radiation Corporation. This is equivalent to 7.8 years of normal exposure.

Each of the six labeled test material sample parts were then divided into smaller pieces for subsequent sampling. A representative piece of each sample part was removed for % MMA residual monomer analysis. % MMA monomer was measured by dissolving the entire piece of test material in acetone and performing GC analysis for MMA monomer content. All other sample pieces of test material were placed into separate glass containers filled with USP saline solution for extraction at 37±4° C. (similar to the environment within the natural eye). Representative extract samples were removed at various time periods throughout the 21-day extraction, i.e., days 4 through 7, days 12 and 13, and days 19 and 20, and subjected to GC analysis for determination of % extracted MMA monomer. The ratio of aqueous to acrylic was 30 to 1.

Tables 2 through 8 contain the results of these studies.

TABLE 2

% RESIDUAL MMA MONOMER LEVELS IN TEST MATERIAL SAMPLES PRIOR TO LEACHING

| Sample Identification | % MMA Monomer |
|---|---|
| UVIA EXPOSED | .46% |
| UVIA UNEXPOSED | .42% |
| UVIIA EXPOSED | .45% |
| UVIIA UNEXPOSED | .47% |
| UVIIIA EXPOSED | .43% |
| UVIIIA UNEXPOSED | .43% |

TABLE 3

RESIDUAL MMA MONOMER IN EXTRACT AND % UV TRANSMISSION OF TEST MATERIAL SAMPLE AND EXTRACT
TEST SAMPLE IDENTIFICATION: UVIA-EXPOSED

| Day | % UV Transmission of Test Material at 390 nm | Thickness of Test Material | % UV Transmission Normalized to .705 mm | % UV Transmission of Extract at 350 nm | % MMA Residual in Extract** |
|---|---|---|---|---|---|
| 0 | 6.0 | .68 | 5.4 | 88.7* | |
| 5 | 6.2 | .679 | 5.6 | 90.0 | ND |
| 6 | 5.6 | .679 | 5.0 | 88.0 | ND |
| 12 | 5.3 | .729 | 5.8 | 87.0 | ND |
| 13 | 5.1 | .728 | 5.6 | 89.0 | ND |
| 19 | 5.7 | .705 | 5.7 | 89.3 | ND |
| 20 | 5.0 | .705 | 5.0 | 88.8 | ND |

*88.7% is the UV transmission of saline solution at 350 nm.
**Detection Limit: 60 ppm MMA monomer to aqueous.

TABLE 4

RESIDUAL MMA MONOMER IN EXTRACT AND % UV TRANSMISSION OF TEST MATERIAL SAMPLE AND EXTRACT
TEST SAMPLE IDENTIFICATION: UVIA-UNEXPOSED

| Day | % UV Transmission of Test Material at 390 nm | Thickness of Test Material | % UV Transmission Normalized to .705 mm | % UV Transmission of Extract at 350 nm | % MMA Residual in Extract** |
|---|---|---|---|---|---|
| 0 | 6.8 | .670 | 5.9 | 88.7* | |
| 6 | 6.8 | .670 | 5.9 | 85.2 | ND |
| 7 | 6.5 | .680 | 5.9 | 83.5 | ND |
| 13 | 6.7 | .669 | 5.8 | 88.8 | ND |

*88.7% is the UV transmission of saline solution at 350 nm.
**Detection Limit: 60 ppm MMA monomer to aqueous.

TABLE 5

RESIDUAL MMA MONOMER IN EXTRACT AND % UV TRANSMISSION OF TEST MATERIAL SAMPLE AND EXTRACT
TEST SAMPLE IDENTIFICATION: UVIIA-EXPOSED

| Day | % UV Transmission of Test Material at 390 nm | Thickness of Test Material | % UV Transmission Normalized to .705 mm | % UV Transmission of Extract at 350 nm | % MMA Residual in Extract** |
|---|---|---|---|---|---|
| 0 | 5.7 | .68 | 5.1 | 88.7* | |
| 4 | 5.3 | .718 | 5.6 | 88.8 | ND |
| 5 | 4.8 | .722 | 5.2 | 90.0 | ND |
| 6 | 5.1 | .722 | 5.5 | 88.7 | ND |
| 18 | 6.0 | .695 | 5.7 | 89.7 | ND |
| 20 | 5.7 | .695 | 5.5 | 90.2 | ND |

*88.7% is the UV transmission of saline solutionat 350 nm.
**Detection Limit: 60 ppm MMA monomer to aqueous.

TABLE 6

RESIDUAL MMA MONOMER IN EXTRACT AND % UV TRANSMISSION OF TEST MATERIAL SAMPLE AND EXTRACT
TEST SAMPLE IDENTIFICATION: UVIIA-UNEXPOSED

| Day | % UV Transmission of Test Material at 390 nm | Thickness of Test Material | % UV Transmission Normalized to .705 mm | % UV Transmission of Extract at 350 nm | % MMA Residual in Extract** |
|---|---|---|---|---|---|
| 0 | 5.7 | .68 | 5.1 | 88.7* | |
| 12 | 6.4 | .680 | 5.8 | 88.3 | ND |
| 13 | 5.6 | .682 | 5.1 | 88.5 | ND |
| 19 | 5.8 | .678 | 5.2 | 89.4 | ND |
| 20 | 6.4 | .677 | 5.7 | 88.5 | ND |

*88.7% is the UV transmission of saline solution at 350 nm.
**Detection Limit: 60 ppm MMA monomer to aqueous.

TABLE 7

RESIDUAL MMA MONOMER IN EXTRACT AND % UV TRANSMISSION OF TEST MATERIAL SAMPLE AND EXTRACT
TEST SAMPLE IDENTIFICATION: UVIIIA-EXPOSED

| Day | % UV Transmission of Test Material at 390 nm | Thickness of Test Material | % UV Transmission Normalized to .705 mm | % UV Transmission of Extract at 350 nm | % MMA Residual in Extract** |
|---|---|---|---|---|---|
| 0 | 6.4 | .65 | 5.1 | 88.7* | |
| 4 | 4.0 | .750 | 4.8 | 88.5 | ND |
| 5 | 4.0 | .745 | 4.8 | 90.0 | ND |
| 12 | 5.0 | .740 | 5.8 | 87.7 | ND |
| 13 | 5.0 | .739 | 5.7 | 89.5 | ND |
| 18 | 5.5 | .710 | 5.6 | 89.7 | ND |
| 20 | 5.3 | .710 | 5.4 | 89.7 | ND |

*88.7% is the UV transmission of saline solution at 350 nm.
**Detection Limit: 60 ppm MMA monomer to aqueous.

TABLE 8

RESIDUAL MMA MONOMER IN EXTRACT AND % UV TRANSMISSION OF TEST MATERIAL SAMPLE AND EXTRACT
TEST SAMPLE IDENTIFICATION: UVIIIA-UNEXPOSED

| Day | % UV Transmission of Test Material at 390 nm | Thickness of Test Material | % UV Transmission Normalized to .705 mm | % UV Transmission of Extract at 350 nm | % MMA Residual in Extract** |
|---|---|---|---|---|---|
| 6 | 5.0 | .718 | 5.3 | 89.0* | |
| 12 | 4.9 | .715 | 5.1 | 89.0 | ND |
| 14 | 4.9 | .714 | 5.1 | 89.0 | ND |
| 19 | 5.5 | .713 | 5.7 | 88.4 | ND |
| 20 | 4.9 | .715 | 5.1 | 88.5 | ND |

*88.7% is the UV transmission of saline solution at 350 nm.
**Detection Limit: 60 ppm MMA monomer to aqueous.

As shown in Table 2, residual MMA monomer at time zero was significantly low for all test material samples. In addition, as shown in Tables 3–8, residual MMA monomer could not be detected in any of the extract samples. Thus, the results of the tests of Examples 2 and 3 indicate that MMA monomer leaching from materials prepared in accordance with Example 1 is not a problem.

EXAMPLE 4

PERMASORB MA LEACHING DETERMINED BY SPECTRAPHOTOMETRIC MEASUREMENTS OF UV TRANSMISSION OF EXTRACTS

The amount of PERMASORB MA that leaches from materials prepared in accordance with Example 1 (test material) was determined by subjecting such test materials to 20 days saline extraction and then measuring the before and after UV transmission of the extract.

The test of this Example was run in conjunction with Example 3 described above. However, subsequent to the initiation of the extraction time period, the following procedure was followed: Representative sample test material pieces and extract samples from each glass container were removed at various time periods throughout the 21-day extraction, i.e., days 4 through 7, days 12 and 13, and days 19 and 20. For each test material sample removed, its thickness and % UV transmission were measured. For each extract sample removed, a measurement of the % UV transmission was performed. The UV spectrophotometer is repeatable to ±1% providing a method that can reliably quantify 2.2 ppm PERMASORB MA. The sensitivity of the instrument is 0.7 ppm.

To further support this analysis, additional samples of the extract solutions were removed on various days throughout the 21-day extraction period and submitted to an independent testing laboratory for High Performance Liquid Chromatography (HPLC) analysis. Utilizing HPLC, the extract solution is subjected to a more severe detection method which can reliably quatify 0.1 ppm PERMASORB MA in the presence of 0.5% monomer and the presence of 0.5 ppm benzoic acid.

Tables 3 through 8 contain the results of these studies (excluding the results of the HPLC determination). In general, if the PERMASORB MA was being extracted, increased absorption of the saline extract solutions would be anticipated. At the same time, increased transmission of the test material samples would be anticipated. Upon review of the data, neither of these two observations occurred with any significance. In fact, after correction for thickness variation of material samples (i.e., normalizing each sample), the differences in % UV transmission can be attributed to the accuracy (±1%) of the UV spectrophotometer. There was no significant difference in the UV transmission spectra of the saline solution extract samples. This was the case both for the test materials that were not exposed to UV radiation and also for the materials that were exposed.

Additionally, the HPLC analysis of the extracts from leached test materials (both irradiation exposed and non-exposed) showed no detectable UV absorber after a total of 19 days leaching at 37° C.±4° C.

EXAMPLE 5

DETERMINATION OF THE AMOUNT OF UNREACTED PERMASORB MA IN MATERIALS PREPARED IN ACCORDANCE WITH EXAMPLE 1

Eight (8) samples of cast material prepared in accordance with Example 1 (test material) were used. Four of the eight (8) samples of test material were sterilized by ethylene oxide sterilization.

All test material samples were placed in a 10 ml vial and then dissolved in HPLC grade acetone for 24 hours at room temperature. All sample vials were sealed with a teflon septum. (Note: To accelerate solution, some samples were subjected to ultrasonification at 65° C. This was sometimes necessary due to the degree of cross-linking.)

The resultant samples were then subjected to HPLC for unreacted PERMASORB MA. The detection limit for this test was 7 ppm. The results of this test are listed in Table 9.

TABLE 9

| Test Sample | PERMASORB MA (ppm) |
|---|---|
| 1. (sterilized) | 7 |
| 2. (non-sterilized) | ND |
| 3. (non-sterilized) | ND |
| 4. (sterilized) | ND |
| 5. (non-sterilized) | 7 |
| 6. (non-sterilized) | ND |
| 7. (sterilized) | 8 |
| 8. (sterilized) | 9 |

Under worst case conditions, i.e., completely dissolving the test material sample in organic solvent and utilizing HPLC (possibly the most severe and sensitive test for UV absorber detection), the highest level of unreacted PERMASORB MA found was 9 ppm. This data, along with previous leachability data using isotonic saline solution as an extracting medium, indicates that leachability of PERMASORB MA is not a problem. This is the case for materials that are not subjected to ethylene oxide sterilization, as well as for materials that are ethylene oxide sterilized.

EXAMPLE 6

DETERMINATION OF RESIDUAL AZOISOBUTYLNITRILE IN MATERIALS PREPARED IN ACCORDANCE WITH EXAMPLE 1

Three samples of materials prepared in accordance with Example 1 were tested for azoisobutylnitrile utilizing wet chemistry techniques (ARLI Method 600-104). The results of the tests are listed in Table 10.

TABLE 10

| Sample | AIBN, g/100 ml |
|---|---|
| XP-30-81-0041/0032 | <0.008 |
| XP-30-81-0041/0045 | <0.008 |
| XP-30-81-0041/0047 | <0.008 |

The conclusion was that no AIBN was in any of the samples. Thus, AIBN leachability from materials prepared in accordance with Example 1 is not a problem.

EXAMPLE 7

PHOTODEGRADATION OF MATERIALS PREPARED IN ACCORDANCE WITH EXAMPLE 1

To determine if photodegradation of material prepared in accordance with Example 1 (test material) could occur, such materials were subjected to high dosage ultraviolet radiation. The materials were subjected to two levels of exposure; the first level was equivalent to 7.8 years of normal eye exposure to UV radiation and the second level was equivalent to 14.5 years. The UV radiation exposed samples were evaluated for any increase in residual MMA monomer, changes in their UV transmission characteristics, and the extent, if any, of changes in PERMASORB MA and MMA leachability rates compared to non-UV exposed control material.

The results of the 7.8 year and 14.5 year ultraviolet exposure tests showed no changes between the before and after exposed test material samples. The residual monomer in the samples both before and after exposure were the same; the ultraviolet transmission of the material before and after exposure to high dosages of UV radiation remained unchanged; and there was no difference in the monomer leachabilty, i.e., none detected, on the before and after exposure samples. The same results were found with regard to the PERMASORB MA leachability of the samples, i.e., none detected.

In addition to the analytical tests set forth in Examples 2–7, which indicated that leaching is not a problem, various in-vivo and in-vitro biological tests were conducted by an independent testing laboratory on materials prepared in accordance with Example 1 to confirm that such materials are biologically compatible with body tissue and fluids.

EXAMPLE 8

ACUTE SYSTEMIC TOXICITY—T 12/4 (CURRENT USP)

Healthy, young, white mice ranging in body weight from 17 to 23 grams were injected either intravenously or intraperitoneally with one of four different extracts (saline, alcohol/saline, polyethylene glycol 400, and cottonseed oil) of a material prepared in accordance with Example 1. The extracts were prepared at 121° C. for one hour. Two groups, each consisting of five mice, were used for each extract. One group was injected with the extract of the test material, while the other group was injected with a blank. After injection, the animals were observed immediately and at 4, 24, 48, and 72 hours. Initial and final body weights were recorded, as well as mortalities and/or reactions. If, during the observation period, none of the animals treated with the extract of the test material show a significantly greater reaction than the animals treated with the blank, the material meets the requirements of the test. The results of the tests are recorded in Table 11.

TABLE 11

| | Mortality and Body Weight Data | | | | | | |
|---|---|---|---|---|---|---|---|
| | TEST MATERIAL | | | | BLANK | | |
| Extract Dose and Route | Animal Number | Weight (gms) Day 0 | Day 3 | # Dead # Tested | Animal Number | Weight (gms) Day 0 | Day 3 | # Dead # Tested |
| Sodium Chloride | 1 | 22 | 23 | 0/5 | 1 | 21 | 21 | 0/5 |
| Injection | 2 | 20 | 23 | | 2 | 21 | 25 | |
| (I.V.: 50 ml/kg) | 3 | 22 | 22 | | 3 | 22 | 24 | |
| | 4 | 21 | 22 | | 4 | 22 | 25 | |
| | 5 | 19 | 23 | | 5 | 20 | 24 | |
| Ethanol in Sodium | 1 | 19 | 21 | 0/5 | 1 | 19 | 23 | 0/5 |
| Chloride Injection (1:20) | 2 | 17 | 21 | | 2 | 19 | 23 | |
| (I.V.: 50 ml/Kg) | 3 | 19 | 23 | | 3 | 22 | 24 | |
| | 4 | 18 | 21 | | 4 | 19 | 23 | |
| | 5 | 19 | 21 | | 5 | 19 | 21 | |
| Polyethylene Glycol 400 | 1 | 19 | 20 | 0/5 | 1 | 18 | 21 | 0/5 |
| (I.P.: 10 g/Kg | 2 | 18 | 21 | | 2 | 19 | 23 | |
| | 3 | 21 | 25 | | 3 | 20 | 24 | |
| | 4 | 21 | 25 | | 4 | 20 | 25 | |
| | 5 | 19 | 21 | | 5 | 19 | 22 | |
| Cottonseed Oil | 1 | 19 | 25 | 0/5 | 1 | 18 | 23 | 0/5 |
| (I.P.: 50 ml/Kg) | 2 | 21 | 26 | | 2 | 18 | 23 | |
| | 3 | 22 | 25 | | 3 | 21 | 25 | |
| | 4 | 20 | 22 | | 4 | 19 | 22 | |
| | 5 | 19 | 21 | | 5 | 21 | 26 | |

The results indicated that there was no significant evidence of acute toxicity with the eluates.

EXAMPLE 9

INTRACUTANEOUS TOXICITY—T 13/4 (CURRENT USP)

Rabbits received a series of intracutaneous injections with up to four extracts (saline, alcohol/saline, polyethylene glycol 400, and cottonseed oil) of materials prepared in accordance with Example 1. The extracts were prepared at 121° C. for 1 hour. Two healthy, previously unused New Zealand white rabbits were used as test animals for each extract. Animals were housed individually and allowed food and water ad libitum. Prior to injection, the hair was closely clipped from the back and flanks of each rabbit. Exactly 0.2 ml of the extract of the test material was injected intracutaneously into ten separate sites on the right side of the back of each animal, while 0.2 ml of the extracting medium (blank) was injected into five separate sites on the left side. Injection sites were examined 24, 48, and 72 hours after injection for erythema and edema. The average tissue reaction to the extract of the test material was compared with the blank. The requirements of the test were met if no significant differences were noted. The results of the tests are recorded in Table 12.

TABLE 12

| Extract | Rabbit No. | 24 HR. ER | 24 HR. ED | 48 HR. ER | 48 HR. ED | 72 HR. ER | 72 HR. ED |
|---|---|---|---|---|---|---|---|
| Sodium Chloride (SC) | | | | | | | |
| Test | 7057 | 0 | 0 | 0 | 0 | 0 | 0 |
| Blank | | 0 | 0 | 0 | 0 | 0 | 0 |
| Test | 7058 | 0 | 0 | 0 | 0 | 0 | 0 |
| Blank | | 0 | 0 | 0 | 0 | 0 | 0 |
| Alcohol in Sodium Chloride 1:20 (AS) | | | | | | | |
| Test | 7059 | 0 | 0 | 0 | 0 | 0 | 0 |
| Blank | | 0 | 0 | 0 | 0 | 0 | 0 |
| Test | 7060 | 0 | 0 | 0 | 0 | 0 | 0 |
| Blank | | 0 | 0 | 0 | 0 | 0 | 0 |
| Polyethylene Glycol 400 (PEG) | | | | | | | |
| Test | 7061 | 0 | 0 | 0 | 0 | 0 | 0 |
| Blank | | 0 | 0 | 0 | 0 | 0 | 0 |
| Test | 7062 | 0 | 0 | 0 | 0 | 0 | 0 |
| Blank | | 0 | 0 | 0 | 0 | 0 | 0 |
| Cottonseed Oil (CSO) | | | | | | | |
| Test | 7063 | 3 | 3 | 3 | 3 | 2 | 2 |
| Blank | | 3 | 3 | 3 | 3 | 2 | 2 |
| Test | 7064 | 3 | 2 | 2 | 2 | 1 | 1 |
| Blank | | 3 | 2 | 2 | 2 | 1 | 1 |

Key
ER = Erythema             ED = Edema

| 0 = None | 0 = None |
|---|---|
| 1 = Barely Perceptible | 1 = Barely Perceptible |
| 2 = Well Defined | 2 = Well Defined |
| 3 = Moderate | 3 = Raised 1 mm |
| 4 = Severe | 4 = Raised >1 mm |

TABLE 12-continued

| $\bar{X}$ Test − $\bar{X}$ Blank = | Δ | Pass | Fail |
|---|---|---|---|
| SC 0 − 0 = | 0 | X | |
| AS 0 − 0 = | 0 | X | |
| PEG 0 − 0 = | 0 | X | |
| CSO 2.3 − 2.3 = | 0 | X | |

The results indicated that there was no significant tissue reaction.

EXAMPLE 10

IMPLANTATION TEST—T 14/7 CURRENT USP)

Two rabbits were implanted with four or more strips (10×1×1 mm) of material prepared in accordance with Example 1 (test material) via needle puncture into the paravertebral muscles. The tissue reaction was evaluated macroscopically after 7 days implantation and compared to a USP control plastic similarly implanted in the same rabbits. The results of the macroscopic evaluation are listed in Table 13.

TABLE 13

Results of Macroscopic Examination: Scoring

| Rabbit | Sample | Test | Control |
|---|---|---|---|
| 6773 | 1 | 1 | 0 |
| | 2 | 1 | 0 |
| | 3 | 0 | 0 |
| | 4 | 0 | 0 |
| | 5 | 0 | 0 |
| 6789 | 1 | 0 | 0 |
| | 2 | 0 | 0 |
| | 3 | 0 | 0 |
| | 4 | 0 | 0 |
| | 5 | 0 | 0 |
| | Mean ($\bar{X}$) | 0.2 | 0.0 |

Scoring Key

| Score | Capsule Formation |
|---|---|
| 0 | None Noted |
| 1 | Up to 0.5 mm |
| 2 | 0.5 to 1.0 mm |
| 3 | 1.0 to 2.0 mm |
| 4 | >2.0 mm |

Reaction Index
$\bar{X}$ (Test) · $\bar{X}$ (Control) = 0.2

| 0–0.5 | Not Significant |
|---|---|
| 0.6–1.0 | Trace |
| 1.1–2.0 | Slight |
| 2.1–3.0 | Moderate |
| >3.1 | Marked |

The results show that there was no significant tissue reaction with the test material as compared to the negative control material.

A microscopic evaluation of the implanted tissue was also conducted 7 days after implantation following routine staining of the tissues with Hematoxylin and Eosin. Tissue reactions were recorded for inflammation, chronic irritation, foreign body response, tissue scarring, and necrosis. The results of the microscopic evaluation are listed in Table 14.

TABLE 14

| | TEST | | CONTROL | | DIFFERENCE |
|---|---|---|---|---|---|
| | 6773 | 6789 | 6773 | 6789 | (Test # − Control) |
| OBSERVATION (0–4) | | | | | |
| Inflammation | | | | | |
| Polymorphonuclear | 0 | 0 | 0 | 0 | |
| Lymphocytes | 1 | 1 | 1 | 1 | |
| Plasma Cells | 0 | 0 | 0 | 0 | |
| Macrophages | 1 | 1 | 1 | 1 | |

TABLE 14-continued

|  | TEST | | CONTROL | | DIFFERENCE |
|---|---|---|---|---|---|
|  | 6773 | 6789 | 6773 | 6789 | (Test # − Control) |
| Giant Cells | 0 | 0 | 0 | 0 | |
| Sub Total (X2) |  | 8 |  | 8 = | 0 |
| Fibroplasia | 2 | 2 | 2 | 2 | |
| Fibrosis | 1 | 1 | 1 | 1 | |
| Fatty Infiltrate | 0 | 0 | 0 | 0 | |
| Necrosis | 0 | 0 | 0 | 0 | |
| Sub Total |  | 6 |  | 6 = | 0 |
| TOTAL |  | TEST: 14 |  | CONTROL: 14 = | 0 |
| Foreign Debris | 0 | 0 | 0 | 0 | |
| Number Sites Examined | 4 | 4 | 2 | 2 | |

Results:
Score Guide (Test − Control): 0 = Non irritant. 1–15 = Slight. 16–30 = Moderate. >30 = Severe for a two rabbit test.

The conclusion, based on the results of both the macroscopic and microscopic tests, is that test material prepared in accordance with Example 1 is a non-irritant.

EXAMPLE 11

OCULAR IRRITATION

Extracts of material prepared in accordance with Example 1 (test material) were injected into the anterior chamber of the eyes of a number of rabbits to determine the irritation or toxicity potential of the extracts.

Three vials of extract of test material exposed to UV radiation were provided and three vials of extract of test material that was not exposed to UV radiation were also provided. Two rabbits were treated from each vial.

Two vials of USP sodium chloride solution (0.9%) were provided as a control solution.

Fifteen healthy rabbits of the New Zealand white variety were selected from the stock colony. (Rabbits weighed 2.4–3.2 kg at initiation). The day before treatment, rabbits were examined by an ophthalmologist with the aid of a slit lamp biomicroscope. Rabbits showing significant abnormalities were replaced. Treatment groups were as follows:

| Group | No. Rabbits | Right Eye | Left Eye |
|---|---|---|---|
| I | 6 | 0.2 ml extract; UV exposed | 0.2 ml control solution |
| II | 6 | 0.2 ml extract; not exposed | 0.2 ml control solution |
| III | 3 | No treatment | No treatment |

Rabbits were anesthetized by intramuscular injection of Acepromazine/Ketamine HCl combination (61 mg/ml) given at a dose of 0.75 ml/kg body weight. Following successful anesthesia, an ocular speculum (lid retractor) was put into place. The eye was steadied by gently grasping the palpebral conjuctiva with a pair of fine-toothed forceps. A 1 cc syringe containing test or control extract and attached to a 27 g needle was introduced into the anterior chamber of the eye. The needle was inserted about 0.5 cm into the anterior chamber at the corneal-scleral junction and parallel to the iris. A second syringe with 27 g needle was inserted at a remote point from the first. Approximately 0.2 ml of the aqueous fluid was evacuated immediately prior to injecting 0.2 ml of test or control extract via the first syringe. After the procedure, rabbits were returned to their cages and allowed to recover.

Three rabbits (Group III) received no treatment and served as negative controls.

Biomicroscope slit lamp examinations were conducted prior to treatment, at day one, day three, and termination (McDonald-Shaddock score system). Control animals were examined prior to treatment and at termination. Additionally, macroscopic observations of the eyes were conducted daily (Draize System); body weights were recorded prior to treatment and at termination; and on a representative number of eyes, tonometry readings (Schiotz tonometer) were taken before and after treatments.

After seven (7) days, the rabbits were killed by injection of T-61 Euthanasia Drug. The eyes were quickly removed and placed in 10% neutral buffered formalin for possible histological processing.

The results of slit lamp biomicroscope studies appear in Tables 15 and 16.

TABLE 15

| SLIT LAMP EXAMINATION | | | | | | | | | |
|---|---|---|---|---|---|---|---|---|---|
| Lab No. | | | | Interval: Pre-treat | | Examination By: | | | |
| | CONJUNCTIVA | | | | | | CORNEA | | |
| Rabbit No. | | Congestion | Swelling | Discharge | Aqueous Flare | Iris | Pannus | Opacity | Area | Fluorescein |
| Group I | | | | | | | | | | |
| 0558 | R | 0 | 0 | 0 | 0 | 0 | 0 | 0 | 0 | 0 |
|  | L | 0 | 0 | 0 | 0 | 0 | 0 | 0 | 0 | 1+ |
| 0803 | R | 0 | 0 | 0 | 0 | 0 | 0 | 0 | 0 | 0 |
|  | L | 0 | 0 | 0 | 0 | 0 | 0 | 0 | 0 | 0 |
| 0870 | R | 0 | 0 | 0 | 0 | 0 | 0 | 0 | 0 | 0 |
|  | L | 0 | 0 | 0 | 0 | 0 | 0 | 0 | 0 | 0 |
| 0871 | R | 0 | 0 | 0 | 0 | 0 | 0 | 0 | 0 | 0 |
|  | L | 0 | 0 | 0 | 0 | 0 | 0 | 0 | 0 | 0 |
| 0795 | R | 0 | 0 | 0 | 0 | 0 | 0 | 0 | 0 | 0 |
|  | L | 0 | 0 | 0 | 0 | 0 | 0 | 0 | 0 | 0 |
| 0868 | R | 0 | 0 | 0 | 0 | 0 | 0 | 0 | 0 | 1+ |
|  | L | 0 | 0 | 0 | 0 | 0 | 0 | 0 | 0 | 0 |

TABLE 15-continued
SLIT LAMP EXAMINATION

Group II

| Rabbit No. | | | | | | | | | | |
|---|---|---|---|---|---|---|---|---|---|---|
| 0817 | R | 0 | 0 | 0 | 0 | 0 | 0 | 0 | 0 | 0 |
|  | L | 0 | 0 | 0 | 0 | 0 | 0 | 0 | 0 | 0 |
| 0822 | R | 0 | 0 | 0 | 0 | 0 | 0 | 0 | 0 | 0 |
|  | L | 0 | 0 | 0 | 0 | 0 | 0 | 0 | 0 | 0 |
| 0806 | R | 0 | 0 | 0 | 0 | 0 | 0 | 0 | 0 | 0 |
|  | L | 0 | 0 | 0 | 0 | 0 | 0 | 0 | 0 | 0 |
| 0808 | R | 0 | 0 | 0 | 0 | 0 | 0 | 0 | 0 | 0 |
|  | L | 0 | 0 | 0 | 0 | 0 | 0 | 0 | 0 | 1+ |
| 0814 | R | 0 | 0 | 0 | 0 | 0 | 0 | 0 | 0 | 0 |
|  | L | 0 | 0 | 0 | 0 | 0 | 0 | 0 | 0 | 0 |
| 0824 | R | 0 | 0 | 0 | 0 | 0 | 0 | 0 | 0 | 1+ |
|  | L | 0 | 0 | 0 | 0 | 0 | 0 | 0 | 0 | 0 |

Lab No. _____  Interval: Pre-treat  Examination By: _____

| Rabbit No. | | CONJUNCTIVA | | | Aqueous Flare | Iris | CORNEA | | | |
|---|---|---|---|---|---|---|---|---|---|---|
|  |  | Congestion | Swelling | Discharge |  |  | Pannus | Opacity | Area | Fluorescein |

Group III

| 0809 | R | 0 | 0 | 0 | 0 | 0 | 0 | 0 | 0 | 0 |
|---|---|---|---|---|---|---|---|---|---|---|
|  | L | 0 | 0 | 0 | 0 | 0 | 0 | 0 | 0 | 0 |
| 0810 | R | 0 | 0 | 0 | 0 | 0 | 0 | 0 | 0 | 0 |
|  | L | 0 | 0 | 0 | 0 | 0 | 0 | 0 | 0 | 1+ |
| 0820 | R | 0 | 0 | 0 | 0 | 0 | 0 | 0 | 0 | 0 |
|  | L | 0 | 0 | 0 | 0 | 0 | 0 | 0 | 0 | 0 |

Lab No. _____  Interval: Day 1  Examination By: _____

| Rabbit No. | | CONJUNCTIVA | | | Aqueous Flare | Iris | CORNEA | | |
|---|---|---|---|---|---|---|---|---|---|
|  |  | Congestion | Swelling | Discharge |  |  | Pannus | Opacity | Area |

Group I - Exposed Material

| 0558 | R | 1+ | 0 | 0 | 0 | 1+ | 0 | 0 | 0 |
|---|---|---|---|---|---|---|---|---|---|
|  | L | 2+ | 0 | 0 | 0 | 1+ | 0 | 0 | 0 |
| 0803 | R | 3+ | 0 | 0 | 0 | 2+ | 0 | 0 | 0 |
|  | L | 3+ | 0 | 0 | 0 | 2+ | 0 | 0 | 0 |
| 0870 | R | 0 | 0 | 2+ | 0 | 1+ | 0 | 0 | 0 |
|  | L | 1+ | 0 | 0 | 0 | 1+ | 0 | 0 | 0 |
| 0871 | R | 0 | 0 | 0 | 0 | 0 | 0 | 0 | 0 |
|  | L | 0 | 0 | 0 | 0 | 0 | 0 | 0 | 0 |
| 0795 | R | 3+ | 0 | 0 | 0 | 1+ | 0 | 0 | 0 |
|  | L | 0 | 0 | 0 | 0 | 1+ | 0 | 0 | 0 |
| 0868 | R | 2+ | 0 | 1+ | 0 | 1+ | 0 | 0 | 0 |
|  | L | 0 | 0 | 0 | 0 | 1+ | 0 | 0 | 0 |

Group II - Unexposed Material

| 0817 | R | 0 | 0 | 0 | 0 | 1+ | 0 | 0 | 0 |
|---|---|---|---|---|---|---|---|---|---|
|  | L | 2+ | 0 | 0 | 0 | 1+ | 0 | 0 | 0 |
| 0822 | R | 2+ | 0 | 0 | 0 | 2+ | 0 | 0 | 0 |
|  | L | 2+ | 0 | 0 | 0 | 1+ | 0 | 0 | 0 |
| 0806 | R | 2+ | 0 | 0 | 0 | 2+ | 0 | 0 | 0 |
|  | L | 1+ | 0 | 0 | 0 | 1+ | 0 | 0 | 0 |
| 0808 | R | 3+ | 0 | 0 | 0 | 3+ | 0 | 0 | 0 |
|  | L | 0 | 0 | 0 | 0 | 1+ | 0 | 0 | 0 |
| 0814 | R | 2+ | 0 | 0 | 0 | 2+ | 0 | 0 | 0 |
|  | L | 1+ | 0 | 0 | 0 | 0 | 0 | 0 | 0 |
| *0824 | R | 4+ | 0 | 0 | 0 | 3+ | 0 | 0 | 0 |
|  | L | 0 | 0 | 0 | 1+ | 3+ | 0 | 0 | 0 |

Lab No. _____  Interval: Day 3  Examination By: _____

| Rabbit No. | | CONJUNCTIVA | | | Aqueous Flare | Iris | CORNEA | | |
|---|---|---|---|---|---|---|---|---|---|
|  |  | Congestion | Swelling | Discharge |  |  | Pannus | Opacity | Area |

Group I - Exposed Material

| 0558 | R | 2+ | 0 | 0 | 1+ | 0 | 0 | 0 | 0 |
|---|---|---|---|---|---|---|---|---|---|
|  | L | 2+ | 0 | 0 | 0 | 0 | 0 | 0 | 0 |
| 0803 | R | 2+ | 0 | 0 | 0 | 1+ | 0 | 0 | 0 |
|  | L | 1+ | 0 | 0 | 0 | 1+ | 0 | 0 | 0 |
| 0870 | R | 1+ | 0 | 0 | 1+ | 0 | 0 | 0 | 0 |
|  | L | 0 | 0 | 0 | 0 | 1+ | 0 | 0 | 0 |
| 0871 | R | 0 | 0 | 0 | 0 | 1+ | 0 | 0 | 0 |
|  | L | 1+ | 0 | 0 | 0 | 1+ | 0 | 0 | 0 |
| 0795 | R | 1+ | 0 | 0 | 1+ | 1+ | 0 | 0 | 0 |
|  | L | 2+ | 0 | 0 | 0 | 1+ | 0 | 0 | 0 |
| 0868 | R | 1+ | 0 | 0 | 0 | 1+ | 0 | 0 | 0 |
|  | L | 1+ | 0 | 0 | 0 | 0 | 0 | 0 | 0 |

Group II - Unexposed Material

| 0817 | R | 1+ | 0 | 0 | 0 | 0 | 0 | 0 | 0 |
|---|---|---|---|---|---|---|---|---|---|
|  | L | 2+ | 0 | 0 | 1+ | 0 | 0 | 0 | 0 |
| 0822 | R | 2+ | 0 | 0 | 0 | 0 | 0 | 0 | 0 |
|  | L | 3+ | 0 | 0 | 2+ | 0 | 0 | 0 | 0 |
| 0806 | R | 3+ | 0 | 0 | 1+ | 3+ | 0 | 0 | 0 |
|  | L | 3+ | 0 | 0 | 1+ | 0 | 0 | 1+ | 0 |

TABLE 15-continued

SLIT LAMP EXAMINATION

| | | | | | | | | | |
|---|---|---|---|---|---|---|---|---|---|
| 0808 | R | 2+ | 0 | 0 | 0 | 0 | 0 | 0 | 0 |
| | L | 2+ | 0 | 0 | 0 | 1+ | 0 | 0 | 0 |
| 0814 | R | 2+ | 0 | 0 | 0 | 1+ | 0 | 0 | 0 |
| | L | 2+ | 0 | 0 | 0 | 0 | 0 | 0 | 0 |
| 0824 | R | 3+ | 0 | 0 | 1+ | 2+ | 0 | 0 | 0 |
| | L | 4+ | 0 | 0 | 1+ | 3+ | 0 | 0 | 0 |

Lab No. _____ Interval: 7-Day Terminal  Examination By: _____

| Rabbit No. | | CONJUNCTIVA | | | Aqueous Flare | Iris | CORNEA | | | |
|---|---|---|---|---|---|---|---|---|---|---|
| | | Congestion | Swelling | Discharge | | | Pannus | Opacity | Area | Fluorescein |
| Group I - Exposed Material | | | | | | | | | | |
| 0558 | R | 0 | 0 | 0 | 0 | 0 | 0 | 0 | 0 | 0 |
| | L | 0 | 0 | 0 | 0 | 0 | 0 | 0 | 0 | 0 |
| 0803 | R | 0 | 0 | 0 | 0 | 0 | 0 | 0 | 0 | 0 |
| | L | 1+ | 0 | 0 | 0 | 0 | 0 | 0 | 0 | 0 |
| 0870 | R | 0 | 0 | 0 | 0 | 0 | 0 | 0 | 0 | 0 |
| | L | 0 | 0 | 0 | 0 | 0 | 1+ | 0 | 0 | 0 |
| 0871 | R | 0 | 0 | 0 | 0 | 0 | 0 | 0 | 0 | 0 |
| | L | 0 | 0 | 0 | 0 | 0 | 0 | 0 | 0 | 0 |
| 0795 | R | 0 | 0 | 0 | 0 | 0 | 0 | 0 | 0 | 0 |
| | L | 0 | 0 | 0 | 0 | 0 | 0 | 0 | 0 | 0 |
| 0868 | R | 0 | 0 | 0 | 0 | 0 | 0 | 0 | 0 | 0 |
| | L | 0 | 0 | 0 | 0 | 0 | 0 | 0 | 0 | 0 |
| Group II - Unexposed Material | | | | | | | | | | |
| 0817 | R | 0 | 0 | 0 | 0 | 0 | 0 | 0 | 0 | 0 |
| | L | 1+ | 0 | 0 | 0 | 0 | 0 | 0 | 0 | 0 |
| 0822 | R | 0 | 0 | 0 | 0 | 0 | 0 | 0 | 0 | 0 |
| | L | 0 | 0 | 0 | 0 | 0 | 0 | 0 | 0 | 0 |
| 0806 | R | 0 | 0 | 0 | 0 | 0 | 0 | 0 | 0 | 0 |
| | L | 0 | 0 | 0 | 0 | 0 | 0 | 0 | 0 | 0 |
| 0808 | R | 0 | 0 | 0 | 0 | 0 | 0 | 0 | 0 | 0 |
| | L | 0 | 0 | 0 | 0 | 0 | 0 | 0 | 0 | 0 |
| 0814 | R | 0 | 0 | 0 | 0 | 0 | 0 | 0 | 0 | 0 |
| | L | 0 | 0 | 0 | 0 | 0 | 0 | 0 | 0 | 0 |
| 0824 | R | 0 | 0 | 0 | 0 | 0 | 0 | 0 | 0 | 0 |
| | L | 0 | 0 | 0 | 0 | 0 | 0 | 0 | 0 | 0 |

Lab No. _____ Interval: 7-Day Terminal  Examination By: _____

| Rabbit No. | | CONJUNCTIVA | | | Aqueous Flare | Iris | CORNEA | | | |
|---|---|---|---|---|---|---|---|---|---|---|
| | | Congestion | Swelling | Discharge | | | Pannus | Opacity | Area | Fluorescein |
| Group III - Negative Controls | | | | | | | | | | |
| 0809 | R | 0 | 0 | 0 | 0 | 0 | 0 | 0 | 0 | 0 |
| | L | 0 | 0 | 0 | 0 | 0 | 0 | 0 | 0 | 1+ |
| 0810 | R | 0 | 0 | 0 | 0 | 0 | 0 | 0 | 0 | 0 |
| | L | 0 | 0 | 0 | 0 | 0 | 0 | 0 | 0 | 0 |
| 0820 | R | 0 | 0 | 0 | 0 | 0 | 0 | 0 | 0 | 0 |
| | L | 0 | 0 | 0 | 0 | 0 | 0 | 0 | 0 | 0 |

R = Right Eye
L = Left Eye
*Difficulties were encountered with the right eye at surgery which contributed to these findings.

TABLE 16

ANTERIOR CHAMBER OBSERVATIONS

| Group No. | Rabbit No. | Iris Adhered to Puncture Day | | | Fibrinous Material Day | | | Other |
|---|---|---|---|---|---|---|---|---|
| | | 1 | 3 | 7 | 1 | 3 | 7 | |
| I. | 0558 R | — | X | — | — | — | — | Fold in corneal epithelium |
| | L | X | X | X | — | — | — | distorted pupil Day 3 |
| | 0803 R | X | X | — | — | X | — | Possible cataract starting |
| | L | X | X | X | — | — | X | in left eye |
| | 0870 R | — | — | — | X | — | — | None |
| | L | X | X | X | — | — | — | |
| | 0871 R | — | X | X | — | — | — | |
| | L | — | X | — | — | — | — | Corneal irregularity day 3 |
| | 0795 R | X | X | — | X | — | — | None |
| | L | X | X | — | — | — | — | |
| | 0868 R | — | X | X | X | — | — | None |
| | L | X | X | X | — | — | — | |
| II. | 0817 R | X | X | — | — | — | — | |
| | L | X | X | — | — | — | — | pupil distorted day 7 |
| | 0822 R | X | X | — | X | — | — | None |
| | L | X | X | X | X | — | — | |
| | 0806 R | X | X | X | X | X | — | Possible cataract starting |
| | L | X | X | — | — | — | — | in right eye |
| | 0808 R | X | X | — | X | — | — | None |
| | L | X | — | — | X | — | — | |

TABLE 16-continued

| | | ANTERIOR CHAMBER OBSERVATIONS | | | | | | |
| | | Iris Adhered to Puncture | | | Fibrinous Material | | | |
| Group No. | Rabbit No. | Day | | | | | | |
| | | 1 | 3 | 7 | 1 | 3 | 7 | Other |
| | 0814 R | X | X | X | X | — | — | None |
| | L | — | X | — | — | X | — | |
| | 0824 R | — | X | X | X | X | X | |
| | L | X | X | X | X | X | X | Distorted Pupil Day 3, 7 |

R = Right Eye (Test)
L = Left Eye (Treated Control)

The McDonald-Shaddock score system used to prepare Tables 15 and 16 follows:

Conjunctival Congestion

0 = Normal. May appear blanched to reddish pink without perilimbal injection (except at 12:00 and 6:00 o'clock positions) with vessels of the palpebral and bulbar conjunctiva easily observed.

+1 = A flushed, reddish color predominately confined to the palpebral conjunctival with some perilimbal injection, but primarily confined to the lower and upper parts of the eye from the 4:00 and 7:00 and 11:00 to 1:00 o'clock positions.

+2 = Bright red color of the palpebral conjunctiva with accompanying perilimbal injection covering at least 75% of the circumference of the perilimbal region.

+3 = Dark, beefy red color with congestion of both the bulbar and the palpebral conjunctiva along with pronounced perilimbal injection and the presence of petechia on the conjunctiva. The petechia generally predominates along the nictitating membrane and the upper palpebral conjunctiva.

Conjunctival Swelling

0 = Normal or no swelling of the conjunctival tissue.

+1 = Swelling above normal without eversion of the lids (can be easily ascertained by noting that the upper and lower eyelids are positioned as in the normal eye); swelling generally starts in the lower cul-de-sac near the inner canthus, which needs slit-lamp examination.

+2 = Swelling with misalignment of the normal approximation of the lower and upper eyelids; primarily confined to the upper eyelid so that in the initial stages the misapproximation of the eyelids begins by partial eversion of the upper eyelid (FIG. 2). In this stage, swelling is confined generally to the upper eyelid, although it exists in the lower cul-de-sac (observed best with the slit lamp).

+3 = Swelling definite with partial eversion of the upper and lower eyelids essentially equivalent. This can be easily ascertained by looking at the animal head-on and noticing the positioning of the eyelids; if the eye margins do not meet, eversion has occurred.

+4 = Eversion of the upper eyelid is pronounced with less pronounced eversion of the lower eyelid. It is difficult to retract the lids and observe the perilimbal region.

Conjunctival Discharge

Discharge is defined as a whitish, gray precipitate, which should not be confused with the small amount of clear, inspisated, mucoid material that can be formed in the medial canthus of a substantial number of rabbit eyes. This material can be removed with a cotton swab before the animals are used.

0 = Normal. No discharge.

+1 = Discharge above normal and present on the inner portion of the eye, but not on the lids or hairs of the eyelids. One can ignore the small amount that is in the inner and outer canthus if it has not been removed prior to starting the study.

+2 = Discharge is abundant, easily observed, and has collected on the lids and around the hairs of the eyelids.

+3 = Discharge has been flowing over the eyelids so as to wet the hairs substantially on the skin around the eye.

Cornea

The scoring scheme measures the severity of corneal cloudiness and the area of the cornea involved. Severity of corneal cloudiness is graded as follows.

0 = Normal cornea. Appears with the slit lamp as having a bright gray line on the epithelial surface and a bright gray line on the endothelial surface with a marblelike gray appearance of the stroma.

+1 = Some loss of transparency. Only the anterior half of the stroma is involved as observed with an optical section of the slit lamp. The underlying structures are clearly visible with diffuse illumination, although some cloudiness can be readily apparent with diffuse illumination.

+2 = Moderate loss of transparency. In addition to involving the anterior stroma, the cloudiness extends all the way to the endothelium. The stroma has lost its marblelike appearance and is homogeneously white. With diffuse illumination, underlying structures are clearly visible.

+3 = Involvement of the entire thickness of the stroma. With optical section, the endothelial surface is still visible. However, with diffuse illumination, the underlying structures are just barely visible (to the extent that the observer is still able to grade flare, iritis, observe for pupillary response, and note lenticular changes).

+4 = Involvement of the entire thickness of the stroma. With the optical section, cannot clearly visualize the endothelium. With diffuse illumination, the underlying structures cannot be seen. Cloudiness removes the capability for judging and grading aqueous flare, iritis, lenticular changes, and pupillary response.

The surface area of the cornea relative to the area of cloudiness is divided into five grades from 0 to +4.

0 = Normal cornea with no area of cloudiness.
+1 = 1–25% area of stromal cloudiness.
+2 = 26–50% area of stromal cloudiness.
+3 = 51–75% area of stromal cloudiness.
+4 = 76–100% area of stromal cloudiness.

The use of fluorescein is a valuable aid in defining epithelial damage.

0 = Absence of fluorescein staining.

+1=Slight fluorescein staining confined to a small focus. With diffuse illumination, the underlying structures are easily visible. (The outline of the pupillary margin is as if there were no fluorescein staining.)
+2=Moderate fluorescein staining confined to a small focus. With diffuse illumination, the underlying structures are clearly visible, although there is some loss of detail.
+3=Marked fluorescein staining. Staining may involve a larger portion of the cornea. With diffuse illumination, underlying structures are barely visible, but are not completely obliterated.
+4=Extreme fluorescein staining. With diffuse illumination, the underlying structures cannot be observed.

Aqueous Flare

The intensity of the Tyndall phenomenon is scored by comparing the normal Tyndall effect observed when the slit-lamp beam passes through the lens with that seen in the anterior chamber. The presence of aqueous flare is presumptive evidence of breakdown of the blood-aqueous barrier.
0=Absence of visible light beam light in the anterior chamber (no Tyndall effect).
+1=The Tyndall effect is barely discernible. The intensity of the light beam in the anterior chamber is less than the intensity of the slit beam as it passes through the lens.
+2=The Tyndall beam in the anterior chamber is easily discernible and is equal in intensity to the slit beam as it passes through the lens.
+3=The Tyndall beam in the anterior chamber is easily discernible; its intensity is greater than the intensity of the slit beam as it passes through the lens.

Iris Involvement

In the following definitions, the primary, secondary, and tertiary vessels are utilized as an aid to determining a subjective ocular score for iris involvement. The assumption is made that the greater the hyperemia of the vessels and the more the secondary and tertiary vessels are involved, the greater the intensity of iris involvement. The scores range from 0 to +4.
0=Normal iris without any hyperemia of the iris vessels. Occasionally around the 12:00 to 1:00 o'clock position near the pupillary border and the 6:00 and 7:00 o'clock position near the pupillary border, there is a small area around 1-3 mm in diameter in which both the secondary and tertiary vessels are slightly hyperemic.
+1=Minimal injection of secondary vessels, but not tertiary. Generally, it is uniform, but may be of greater intensity at the 1:00 or 6:00 o'clock position. If it is confined to the 1:00 or 6:00 o'clock position, the tertiary vessels must be substantially hyperemic.
+2=Minimal injection of tertiary vessels and minimal to moderate injection of the secondary vessels.
+3=Moderate injection of the secondary and tertiary vessels with slight swelling of the iris stroma (this gives the iris surface a slightly rugose appearance, which is usually most prominent near the 3:00 and 9:00 o'clock positions).
+4=Marked injection of the secondary and tertiary vessels with marked swelling of the iris stroma. The iris appears rugose; may be accompanied by hemorrhage (hyphema) in the anterior chamber.

Pannus is vascularization or the penetration of new blood vessels into the corneal stroma. The vessels are derived from the limbal vascular loops. Pannus is divided into three grades.
0=No pannus.
+1=Vascularization is present, but vessels have not invaded the entire corneal circumference. Where localized vessel invasion has occurred, they have not penetrated beyond 2 mm.
+2=Vessels have invaded 2 mm or more around the entire corneal circumference.

As a result of the biomicroscopic study (Tables 15 and 16), no significant differences were noted between the test and control eyes of the treated animals. The anterior chamber of both eyes showed typical post-surgical changes such as iritis and an occasional aqueous flare. Observations were most acute at 24 hours after surgery. There were many cases of irido-corneal touch related to the injection procedure. The area of iris touch, in all cases, was to the healing injection sites. This observation was more prevalent at days 1 and 3.

A number of eyes had evidence of fibrinous material in the anterior chamber. This observation was believed to be related to surgical trauma.

One test eye and one control eye showed evidence of early cataract formation due to trauma.

Slight corneal scarring was noted at most needle puncture sites. At seven (7) days post-surgery, all changes had decreased significantly in severity and many eyes were quite normal in appearance. Some irido-corneal touch and pin-point corneal opacities were still present at the injection sites.

Macroscopic observations recorded daily appear in Table 17.

TABLE 17

MACROSCOPIC OBSERVATIONS SUMMARY OF OCULAR SCORES
(Draize System)

| | Day 1 | | Day 2 | | Day 3 | | Day 4 | | Day 5 | | Day 6 | | Day 7 | |
|---|---|---|---|---|---|---|---|---|---|---|---|---|---|---|
| | T | C | T | C | T | C | T | C | T | C | T | C | T | C |
| Lab No. | | | | | | | | | | | | | | |
| Group I - (Exposed) | | | | | | | | | | | | | | |
| NO: 0558 | | | | | | | | | | | | | | |
| Cornea (X5) | 0 | 0 | 0 | 0 | 0 | 0 | 0 | 0 | 0 | 0 | 0 | 0 | 0 | 0 |
| Iris Score (X 5) | 5 | 10 | 5 | 10 | 5 | 5 | 0 | 0 | 0 | 0 | 0 | 0 | 0 | 0 |
| Conjunctiva Score (x 2) | 0 | 0 | 0 | 0 | 0 | 0 | 0 | 0 | 0 | 0 | 0 | 0 | 0 | 0 |
| Total Score | 5 | 10 | 5 | 10 | 5 | 5 | 0 | 0 | 0 | 0 | 0 | 0 | 0 | 0 |
| NO: 0803 | | | | | | | | | | | | | | |
| Cornea (X5) | 0 | 0 | 0 | 0 | 0 | 0 | 0 | 0 | 0 | 0 | 0 | 0 | 0 | 0 |
| Iris Score (X 5) | 10 | 10 | 10 | 10 | 10 | 5 | 5 | 5 | 5 | 5 | 0 | 0 | 0 | 0 |
| Conjunctiva Score (x 2) | 0 | 0 | 0 | 0 | 0 | 0 | 0 | 0 | 0 | 0 | 0 | 0 | 0 | 0 |
| Total Score | 10 | 10 | 10 | 10 | 10 | 5 | 5 | 5 | 5 | 5 | 0 | 0 | 0 | 0 |

TABLE 17-continued

MACROSCOPIC OBSERVATIONS SUMMARY OF OCULAR SCORES
(Draize System)

| | Days: 1 | | 2 | | 3 | | 4 | | 5 | | 6 | | 7 | |
|---|---|---|---|---|---|---|---|---|---|---|---|---|---|---|
| | T | C | T | C | T | C | T | C | T | C | T | C | T | C |
| NO: 0870 | | | | | | | | | | | | | | |
| Cornea (X5) | 0 | 0 | 0 | 0 | 0 | 0 | 0 | 0 | 0 | 0 | 0 | 0 | 0 | 0 |
| Iris Score (X 5) | 10 | 5 | 10 | 5 | 5 | 5 | 0 | 0 | 0 | 0 | 0 | 0 | 0 | 0 |
| Conjunctiva Score (x 2) | 2 | 0 | 0 | 0 | 0 | 0 | 0 | 0 | 0 | 0 | 0 | 0 | 0 | 0 |
| Total Score | 12 | 5 | 10 | 5 | 5 | 5 | 0 | 0 | 0 | 0 | 0 | 0 | 0 | 0 |
| NO: 0871 | | | | | | | | | | | | | | |
| Cornea (X5) | 0 | 0 | 0 | 0 | 0 | 0 | 0 | 0 | 0 | 0 | 0 | 0 | 0 | 0 |
| Iris Score (X5) | 0 | 0 | 0 | 0 | 0 | 0 | 0 | 0 | 0 | 0 | 0 | 0 | 0 | 0 |
| Conjunctiva Score (x 2) | 0 | 0 | 0 | 0 | 0 | 0 | 0 | 0 | 0 | 0 | 0 | 0 | 0 | 0 |
| Total Score | 0 | 0 | 0 | 0 | 0 | 0 | 0 | 0 | 0 | 0 | 0 | 0 | 0 | 0 |
| 0795 | | | | | | | | | | | | | | |
| Cornea (X5) | 0 | 0 | 0 | 0 | 0 | 0 | 0 | 0 | 0 | 0 | 0 | 0 | 0 | 0 |
| Iris Score (X 5) | 10 | 5 | 10 | 5 | 5 | 5 | 0 | 5 | 0 | 0 | 0 | 0 | 0 | 0 |
| Conjunctiva Score (x 2) | 0 | 0 | 0 | 0 | 0 | 0 | 0 | 0 | 0 | 0 | 0 | 0 | 0 | 0 |
| Total Score | 10 | 5 | 10 | 5 | 5 | 5 | 0 | 5 | 0 | 0 | 0 | 0 | 0 | 0 |
| 0863 | | | | | | | | | | | | | | |
| Cornea (X5) | 0 | 0 | 0 | 0 | 0 | 0 | 0 | 0 | 0 | 0 | 0 | 0 | 0 | 0 |
| Iris Score (X 5) | 5 | 5 | 5 | 5 | 5 | 5 | 0 | 0 | 0 | 0 | 0 | 0 | 0 | 0 |
| Conjunctiva Score (x 2) | 0 | 0 | 0 | 0 | 0 | 0 | 0 | 0 | 0 | 0 | 0 | 0 | 0 | 0 |
| Total Score | 5 | 5 | 5 | 5 | 5 | 5 | 0 | 0 | 0 | 0 | 0 | 0 | 0 | 0 |
| Lab No. Group II - (Not Exposed) | | | | | | | | | | | | | | |
| NO: 0824 | | | | | | | | | | | | | | |
| Cornea (X5) | 0 | 0 | 0 | 0 | 0 | 0 | 0 | 0 | 0 | 0 | 0 | 0 | 0 | 0 |
| Iris Score (X 5) | 10 | 10 | 10 | 10 | 5 | 10 | 5 | 5 | 5 | 5 | 5 | 5 | 0 | 0 |
| Conjunctiva Score (x 2) | 0 | 0 | 0 | 0 | 0 | 0 | 0 | 0 | 0 | 0 | 0 | 0 | 0 | 0 |
| Total Score | 10 | 10 | 10 | 10 | 5 | 10 | 5 | 5 | 5 | 5 | 5 | 5 | 0 | 0 |
| NO:0817 | | | | | | | | | | | | | | |
| Cornea (X5) | 0 | 0 | 0 | 0 | 0 | 0 | 0 | 0 | 0 | 0 | 0 | 0 | 0 | 0 |
| Iris Score (X 5) | 5 | 5 | 5 | 5 | 5 | 0 | 0 | 0 | 0 | 0 | 0 | 0 | 0 | 0 |
| Conjunctiva Score (x 2) | 0 | 0 | 0 | 0 | 0 | 0 | 0 | 0 | 0 | 0 | 0 | 0 | 0 | 0 |
| Total Score | 5 | 5 | 5 | 5 | 5 | 0 | 0 | 0 | 0 | 0 | 0 | 0 | 0 | 0 |
| NO: 0822 | | | | | | | | | | | | | | |
| Cornea (X5) | 0 | 0 | 0 | 0 | 0 | 0 | 0 | 0 | 0 | 0 | 0 | 0 | 0 | 0 |
| Iris Score (X 5) | 0 | 0 | 0 | 0 | 0 | 0 | 0 | 0 | 0 | 0 | 0 | 0 | 0 | 0 |
| Conjunctiva Score (x 2) | 0 | 0 | 0 | 0 | 0 | 0 | 0 | 0 | 0 | 0 | 0 | 0 | 0 | 0 |
| Total Score | 0 | 0 | 0 | 0 | 0 | 0 | 0 | 0 | 0 | 0 | 0 | 0 | 0 | 0 |
| NO: 0806 | | | | | | | | | | | | | | |
| Cornea (X5) | 0 | 0 | 0 | 0 | 0 | 0 | 0 | 0 | 0 | 0 | 0 | 0 | 0 | 0 |
| Iris Score (X 5) | 5 | 0 | 5 | 0 | 10 | 0 | 5 | 0 | 5 | 0 | 0 | 0 | 0 | 0 |
| Conjunctiva Score (x 2) | 0 | 0 | 0 | 0 | 0 | 0 | 0 | 0 | 0 | 0 | 0 | 0 | 0 | 0 |
| Total Score | 5 | 0 | 5 | 0 | 10 | 0 | 5 | 0 | 5 | 0 | 0 | 0 | 0 | 0 |
| NO: 0808 | | | | | | | | | | | | | | |
| Cornea (X5) | 0 | 0 | 0 | 0 | 0 | 0 | 0 | 0 | 0 | 0 | 0 | 0 | 0 | 0 |
| Iris Score (X 5) | 10 | 5 | 10 | 5 | 5 | 5 | 0 | 0 | 0 | 0 | 0 | 0 | 0 | 0 |
| Conjunctiva Score (x 2) | 0 | 0 | 0 | 0 | 0 | 0 | 0 | 0 | 0 | 0 | 0 | 0 | 0 | 0 |
| Total Score | 10 | 5 | 10 | 5 | 5 | 5 | 0 | 0 | 0 | 0 | 0 | 0 | 0 | 0 |
| NO: 0814 | | | | | | | | | | | | | | |
| Cornea (X5) | 0 | 0 | 0 | 0 | 0 | 0 | 0 | 0 | 0 | 0 | 0 | 0 | 0 | 0 |
| Iris Score (X 5) | 5 | 5 | 5 | 5 | 0 | 0 | 5 | 0 | 0 | 0 | 0 | 0 | 0 | 0 |
| Conjunctiva Score (x 2) | 0 | 0 | 0 | 0 | 0 | 0 | 0 | 0 | 0 | 0 | 0 | 0 | 0 | 0 |
| Total Score | 5 | 5 | 5 | 5 | 0 | 0 | 5 | 0 | 0 | 0 | 0 | 0 | 0 | 0 |
| Lab No. Group III - Sham-Control | | | | | | | | | | | | | | |
| NO: 0809 | | | | | | | | | | | | | | |
| Cornea (X5) | 0 | 0 | 0 | 0 | 0 | 0 | 0 | 0 | 0 | 0 | 0 | 0 | 0 | 0 |
| Iris Score (X 5) | 0 | 0 | 0 | 0 | 0 | 0 | 0 | 0 | 0 | 0 | 0 | 0 | O | 0 |
| Conjunctiva Score (x 2) | 0 | 0 | 0 | 0 | 0 | 0 | 0 | 0 | 0 | 0 | 0 | 0 | 0 | 0 |
| Total Score | 0 | 0 | 0 | 0 | 0 | 0 | 0 | 0 | 0 | 0 | 0 | 0 | 0 | 0 |
| NO: 0810 | | | | | | | | | | | | | | |
| Cornea (X5) | 0 | 0 | 0 | 0 | 0 | 0 | 0 | 0 | 0 | 0 | 0 | 0 | 0 | 0 |
| Iris Score (X 5) | 0 | 0 | 0 | 0 | 0 | 0 | 0 | 0 | 0 | 0 | 0 | 0 | 0 | 0 |
| Conjunctiva Score (x 2) | 0 | 0 | 0 | 0 | 0 | 0 | 0 | 0 | 0 | 0 | 0 | 0 | 0 | 0 |
| Total Score | 0 | 0 | 0 | 0 | 0 | 0 | 0 | 0 | 0 | 0 | 0 | 0 | 0 | 0 |
| NO: 0820 | | | | | | | | | | | | | | |
| Cornea (X5) | 0 | 0 | 0 | 0 | 0 | 0 | 0 | 0 | 0 | 0 | 0 | 0 | 0 | 0 |
| Iris Score (X 5) | 0 | 0 | 0 | 0 | 0 | 0 | 0 | 0 | 0 | 0 | 0 | 0 | 0 | 0 |
| Conjunctiva Score (x 2) | 0 | 0 | 0 | 0 | 0 | 0 | 0 | 0 | 0 | 0 | 0 | 0 | 0 | 0 |

TABLE 17-continued
MACROSCOPIC OBSERVATIONS SUMMARY OF OCULAR SCORES
(Draize System)

| | Days: | | | | | | | | | | | | |
|---|---|---|---|---|---|---|---|---|---|---|---|---|---|
| | 1 | | 2 | | 3 | | 4 | | 5 | | 6 | | 7 |
| | T | C | T | C | T | C | T | C | T | C | T | C | T | C |
| Total Score | 0 | 0 | 0 | 0 | 0 | 0 | 0 | 0 | 0 | 0 | 0 | 0 | 0 | 0 |

Test - Right
Control - Left

The scale used for scoring ocular lesions as listed in Table 17 is as follows:

(1) Cornea
(A) Opacity-degree of density (area most dense taken for reading)

| | |
|---|---|
| No opacity | 0 |
| Scattered or diffuse area, details of iris clearly visible | 1 |
| Easily discernible translucent areas, details of iris slightly obscured | 2 |
| Opalescent areas, no details of iris visible, size of pupil barely discernible | 3 |
| Opaque, iris invisible | 4 |

(B) Area of cornea involved

| | |
|---|---|
| One quarter (or less) but not zero | 1 |
| Greater than one qluarter, but less than half | 2 |
| Greater than half, but less than three quarters | 3 |
| Greater than three quarters, up to | 4 |

Score equals A × B × 5    Total maximum = 80

(2) Iris
(A) Values

| | |
|---|---|
| Normal | 0 |
| Folds above normal, congestion, swelling, circumcorneal injection (any or all of these or combination of any thereof) iris still reacting to light (sluggish reactions are positive) | 1 |
| No reaction to light, hemorrhage, gross destruction (any or all of these) | 2 |

Score equals A × 5    Total maimum = 10

(3) Conjunctivae
(A) Redness (refers to palpebral and bulbar conjunctivae excluding cornea and iris)

| | |
|---|---|
| Vessels normal | 0 |
| Vessels definitely injected above normal | 1 |
| More diffuse, deeper crimson red, individual vessels not easily discernible | 2 |
| Diffuse beefy red | 3 |

(B) Chemosis

| | |
|---|---|
| No swelling | 0 |
| Any swelling above normal (includes nictitating membrane) | 1 |
| Obvious swelling with partial eversion of lids | 2 |
| Swelling with lids about half closed | 3 |
| Swelling with lids half closed to completely closed | 4 |

(C) Discharge

| | |
|---|---|
| No discharge | 0 |
| Any amount different from normal (does not include small amounts observed in inner canthus of normal animals) | 1 |
| Discharge with moistening of the lids and hairs adjacent to lids | 2 |
| Discharge with moistening of the lids and hairs and considerable area around the eye | 3 |

Score equals A + B + C × 2    Total maximum = 20

The maximum total score is the sum of all scores obtained for the cornea, iris, and conjunctivae. Total maximum score possible =110.

Iritis was the significant observation noted during the macroscopic observations. As the post-operative period progressed, the iritis diminished. At seven (7) days, the gross appearance of the majority of the eyes was similar to the non-treated control group.

Body weights of the test rabbits recorded prior to treatment and at 7 days indicated no appreciable weight loss during the study. Animals remained healthy throughout.

Tonometry readings (Schiotz with standard 5.5 g wt) taken prior to and after treatment indicated that the removal and instillation of approximately equal volumes of fluid caused an immediate increase in intraocular pressure. There was some evidence that the ocular pressure had returned to normal by 7 days, but the influence of general anesthetics and/or euthanasia drug was not determined. The results of the tonometry readings are in Table 18.

TABLE 18

| Group | Rabbit No. | At Surgery Pre | At Surgery Post | At Termination anesthetized | At Termination Euthanized |
|---|---|---|---|---|---|
| I | 0558 R | N.T. | 20+ | N.T. | 12.0 |
| | L | 4.5 | 20+ | N.T. | 10.0 |
| | 0803 R | 6.5 | 20+ | N.T. | 5.0 |
| | L | 5.0 | 20+ | N.T. | 3.0 |
| | 0870 R | 6.5 | 20+ | N.T. | 11.0 |
| | L | 8.0 | 20+ | N.T. | 10.0 |
| II | 0817 R | 6.0 | 20+ | 6.0 | 11.0 |
| | L | N.T. | 20+ | 4.5 | 6.0 |
| | 0822 R | 7.0 | 20+ | 4.5 | 12.0 |
| | L | N.T. | 20+ | 4.5 | 14.0 |
| | 0808 R | 5.5 | 20+ | N.T. | N.T. |
| | L | 6.0 | 20+ | N.T. | N.T. |

N.T. = Not taken.
R = Right eye.
L = Left eye.

EXAMPLE 12
Cytotoxicity—MEM Elution—MG 23

A monolayer of L-929 Mouse Fibroblast cells was grown to confluency and exposed to an extract of a test sample prepared by placing material prepared in accordance with Example 1 (test material) in 20 ml of Minimum Essential Medium (Eagle) and bovine serum (5%) and extracting at 37° C. for 24 hours. An MEM aliquot was used as a negative control. After exposure to the extract, the cells were examined microscopically for cytotoxic effect (CTE). Cytotoxicity was scored as either Non-Toxic (N), Intermediate (I), or Toxic (T). N=Indicates a negative or non-toxic response;

I=Indicates an intermediate response, a subjective assessment of the extent of cellular response; and
T=Indicates a positive or toxic response consisting of greater than 50% cell death.
The results are listed in Table 19.

TABLE 19

| | OBSERVATION PERIOD | | |
|---|---|---|---|
| | 24 Hours | 48 Hours | 72 Hours |
| Test Material | N | N | N |
| Control | N | N | N |

Comments: Positive control toxic at 24 hours.

The results indicate that all samples were non-toxic.

EXAMPLE 13

CYTOTOXICITY—AGAR OVERLAY—MG 26

A monolayer of L-929 Mouse Fibroblast cells was grown to confluency and overlaid with Medium 199 supplemented with serum, antibiotics, neutral red, and agar. An intraocular lens comprising material prepared in accordance with Example 1 (test material) was placed on the solidified overlay surface. Following incubation for 24 hours, the culture was macroscopically examined for evidence of cell decolorization to determine the zone of cell lysis. Any decolorized zone present was examined microscopically to confirm cell lysis. The results are listed in Table 20.

TABLE 20

| | Score | Zone of Lysis (mm) |
|---|---|---|
| Test Material | N | — |
| Negative Control (USP Negative Control Plastic) | N | — |
| Positive Control (Latex) | T | 9 |

N (Non-toxic) No change in cell morphology in proximity to test sample.
T (Toxic) Death and/or degeneration of cells directly beneath the area of test sample and possibly also within a zone extended beyond the test sample. Where a zone of lysis was observed, the distance from the edge of the sample to the edge of the zone was measured and reported in millimeters (mm).

The results indicate that the test material is non-toxic for L-929 cells under the above described test conditions.

EXAMPLE 14

CYTOTOXICITY—AGAR OVERLAY—MG 26

A monolayer of L-929 Mouse Fibroblast cells was grown to confluency and overlaid with Medium 199 supplemented with serum, antibiotics, neutral red, and agar. A 1 cm² sheet of material prepared in accordance with Example 1 (test material) was placed on the solidified overlay surface. Following incubation for 24 hours, the culture was macroscopically examined for evidence of cell decolorization to determine the zone of cell lysis. Any decolorized zone present was examined microscopically to confirm cell lysis. The results are listed in Table 21.

TABLE 21

| | Score | Zone of Lysis (mm) |
|---|---|---|
| Test Material | N | — |
| Negative Control (USP Negative Control Plastic) | N | — |

TABLE 21-continued

| | Score | Zone of Lysis (mm) |
|---|---|---|
| Positive Control (Latex) | T | 8 |

N (Non-toxic) No change in cell morphology in proximity to test sample.
T (Toxic) Death and/or degeneration of cells directly beneath the area of test sample and possibly also within a zone extended beyond the test sample. Where a zone of lysis was observed, the distance from the edge of the sample to the edge of the zone was measured and reported in millimeters (mm).

The results indicate that the test material is non-toxic for L-929 cells under the above described conditions.

EXAMPLE 15

HEMOLYSIS TEST (EXTRACT)

90 square centimeters of material prepared in accordance with Example 1 (test material) was placed in 30 ml of sodium chloride solution (0.9%) and extracted at 121° C. for 1 hour. The extract was divided into two tubes of 10 ml each.

To each tube was added 0.2 ml of human blood previously collected in a vacuum tube containing E.D.T.A. Tubes were inverted gently to mix the contents, then placed in a constant temperature water bath at 37° C. for 1 hour. The blood saline mixture was then transferred to a new set of tubes and centrifuged for 5 minutes at 1,500 RPM. The supernatant liquid was aspirated into a second tube and centrifuged again.

The optical density of each sample solution was determined spectrophotometrically at 545 m$\mu$. Similarly, optical densities were recorded for a positive control (10 ml water and 0.2 ml blood) and a negative control (10 ml Sodium Chloride and 0.2 ml blood). The results are listed in Table 22.

TABLE 22

Negative Control = 0 absorbance = 0% hemolysis.
Positive Control = 1.699 absorbance = 100% hemolysis.
Test #1 = 0 absorbance = 0% hemolysis.
Test #2 = 0 absorbance = 0% hemolysis.
Mean Hemolysis 0%.

The results indicated that the test material is non-hemolytic under conditions of this test.

EXAMPLE 16

HEMOLYSIS TEST (DIRECT)

Sterilized Test Material

Material prepared in accordance with Example 1 (test material) was sterilized with ethylene oxide and cut into small chips or lengths (3 cm×0.5 cm). 2 grams of the test material were placed in each of two extracting tubes containing 10 ml of sodium chloride solution (0.9%).

To each tube was added 0.2 ml of human blood previously collected in a vacuum tube containing E.D.T.A. Tubes were inverted gently to mix the contents, then placed in a constant temperature water bath at 37° C. for 1 hour. The blood saline mixture was then transferred to a new set of tubes and centrifuged for 5 minutes at 1,500 RPM. The supernatant liquid was aspirated into a second tube and centrifuged again.

The optical density of each sample solution was determined spectrophotometrically at 545 m$\mu$. Similarly, optical densities were recorded for a positive control (10 ml water and 0.2 ml blood) and a negative control (10 ml Sodium Chloride and 0.2 ml blood). The results are listed in Table 23.

TABLE 23

Negative Control = 0 absorbance = 0% hemolysis.
Positive Control = 1.699 absorbance = 100% hemolysis.
Test #1 = 0.009 absorbance = 0.5% hemolysis.
Test #2 = 0.004 absorbance = 0.2% hemolysis.
Mean hemolysis 0.4%.

The results indicated that the test material is non-hemolytic under conditions of the test.

EXAMPLE 17

HEMOLYSIS TEST (DIRECT) FINISHED LENS

An intraocular lens comprising Material prepared in accordance with Example 1 (test material) was cut in half. Each half was placed in a separate extracting tube containing 10 ml of sodium chloride solution (0.9%).

To each tube was added 0.2 ml of human blood previously collected in a vacuum tube containing E.D.T.A. Tubes were inverted gently to mix the contents, then placed in a constant temperature water bath at 37° C. for 1 hour. The blood saline mixture was then transferred to a new set of tubes and centrifuged for 5 minutes at 1,500 RPM. The supernatant liquid was aspirated into a second tube and centrifuged again.

The optical density of each sample solution was determined spectrophotometrically at 545 m$\mu$. Similarly, optical densities were recorded for a positive control (10 ml water and 0.2 ml blood) and a negative control (10 ml Sodium Chloride and 0.2 ml blood). The results are listed in Table 24.

TABLE 24

Negative Control = 0 absorbance = 0% hemolysis.
Positive Control = 1.699 absorbance = 100% hemolysis.
Test #1 = 0.004 absorbance = 0.2% hemolysis.
Test #2 = 0.009 absorbance = 0.5% hemolysis.
Mean Hemolysis 0.4%.

The results indicated that the test material is non-hemolytic under conditions of the test.

EXAMPLE 18

HEMOLYSIS TEST (DIRECT)

(Non-sterilized test material)

Material prepared in accordance with Example 1 (test material) was cut into small chips or lengths (3 cm×0.5 cm) and two grams of the material was placed into each of two extracting tubes containing 10 ml of sodium chloride solution (0.9%).

To each tube was added 0.2 ml human blood previously collected in a vacuum tube containing E.D.T.A. Tubes were inverted gently to mix the contents, then placed in a constant temperature water bath at 37° C. for 1 hour. The blood saline mixture was then transferred to a new set of tubes and centrifuged for 5 minutes at 1,500 RPM. The supernatant liquid was aspirated into a second tube and centrifuged again.

The optical density of each sample solution was determined spectrophotometrically at 545 m$\mu$. Similarly, optical densities were recorded for a positive control (10 ml water and 0.2 ml blood) and a negative control (10 ml Sodium Chloride and 0.2 ml blood). The results are listed in Table 25.

TABLE 25

Negative Control = 0 absorbance = 0% hemolysis.
Positive Control = 1.699 absorbance = 100% hemolysis.
Test #1 = 0 absorbance = 0% hemolysis.
Test #2 = 0 absorbance = 0% hemolysis.
Mean Hemolysis 0%.

The results indicated that the test material is non-hemolytic under conditions of the test.

EXAMPLE 19

MUTAGENICITY SCREEN

Materials prepared in accordance with Example 1 (test material) were tested for their ability to cause mutagenic response in bacterial tester stains with and without the presence of an enzomatic activation system. The results of the test are in Table 26.

TABLE 26

| I. Spontaneous Mutation Rate | |
|---|---|
| Strain | Revertants/Plate |
| TA 98 | 26 |
| TA 100 | 198 |
| TA 1537 | 11 |

| II. Mutagen Test | | | | |
|---|---|---|---|---|
| Strain | Sample | Dose/Plate | S-9 Mix | Evaluation |
| TA 98 | Unknown | 10 mm$^2$ | + | Non-mutagenic |
| TA 100 | Unknown | 10 mm$^2$ | + | Non-mutagenic |
| TA 1537 | Unknown | 10 mm$^2$ | + | Non-mutagenic |
| TA 98 | Unknown | 10 mm$^2$ | − | Non-mutagenic |
| TA 100 | Unknown | 10 mm$^2$ | − | Non-mutagenic |
| TA 1537 | Unknown | 10 mm$^2$ | − | Non-mutagenic |
| TA 98 | α-benzo-pyrene | 10 μg | + | Mutagenic |
| TA 100 | α-benzo-pyrene | 10 μg | + | Mutagenic |
| TA 1537 | α-benzo-pyrene | 10 μg | + | Mutagenic |

The conclusion, based on the test results, is that no evidence was found indicating that the test material is mutagenic.

EXAMPLE 20

CELL GROWTH INHIBITION

Nine sample weights of material prepared in accordance with Example 1 (test material) were extracted in distilled water in the following ratios: 4,000 mg/20 ml, 500 mg/20 ml, 100 mg/20 ml, 50 mg/20 ml, 4 mg/20 ml, 3 mg/20 ml, 2 mg/20 ml, 1 mg/20 ml, 1 mg/40 ml. Each sample was extracted at 121° C. for one hour.

For each extract, fifteen mls of each extract was aseptically added to fifteen ml of double strength Minimal Essential Medium (2XMEM) in a sterile container. For each extract, two ml was added to ten assay tubes containing 0.2 ml of L-929 Mouse Fibroblast cells previously adjusted to 10$^6$ cells/ml, then mixed. Ten additional tubes were prepared similarly as controls, substituting distilled water for sample extract solution. Half of the extract treated tubes and half of the control tubes were immediately incubated at 37° C. for 72 hours. The remaining tubes were centrifuged and the medium decanted. The cells were resuspended in sterile Phosphate Buffered Saline (PBS), centrifuged, and the PBS decanted. The cells were resuspended, centrifuged, and decanted twice again, then stored for 72 hours at 4° C. At the end of the incubation period, the tubes at 37° C. were washed in the same manner as the refrigerated tubes. All tubes were assayed for protein content using a phenol reagent and measuring the degree of color development with the aid of a spectrophotometer. The average Optical Density (O. D.) of each set of five replicate tubes was determined and the percent of inhibition of cell growth was calculated as follows:

$$\% ICG = 100 - \left[ 100 \times \frac{(A) - (B)}{(C) - (D)} \right]$$

where:
A=Avg. O. D. 72-hour treated tubes;
B=Avg. O. D. zero time treated tubes;
C=Avg. O. D. 72-hour control tubes;
D=Avg. O. D. zero time control tubes.
The results are listed in Table 27.

TABLE 27

| | Extract | Percent of Cell Growth Inhibition |
|---|---|---|
| 1. | 4,000 mg/20 ml | 0 |
| 2. | 500 mg/20 ml | 0 |
| 3. | 100 mg/20 ml | 0 |
| 4. | 50 mg/20 ml | 0 |
| 5. | 4 mg/20 ml | 0 |
| 6. | 3 mg/20 ml | 0 |
| 7. | 2 mg/20 ml | 0 |
| 8. | 1 mg/20 ml | 0 |
| 9. | 1 mg/40 ml | 0 |

The precision of the assay is approximately ±10%. That is, the range of values expected for a non-toxic biomaterial in the nine point percent ICG assay would fall between ±10% inhibition. All nine extracts fall within this range and, therefore, do not produce inhibition of cell growth.

The above described leaching and in-vivo and in-vitro biological studies indicated that a PMMA/PERMASORB MA co-polymer material prepared in accordance with Example 1 is biocompatible with body tissue and fluids. Thus, an intraocular lens comprising such a material provided in accordance with practice of this invention is suitable for implantation into the eye.

EXAMPLE 21

RADIATION TRANSMITTANCE COMPARISON

PMMA/PERMASORB MA co-polymer materials prepared in accordance with Example 1 were also tested for transmittance of radiation and were compared to: (1) a standard intraocular lens formed of PMMA; (2) a human lens (age 22 years); and (3) a human lens (age 53 years). The results are listed below in Table 28.

TABLE 28
TRANSMITTANCE OF ULTRA-VIOLET LIGHT ABSORBING INTRAOCULAR LENS MATERIAL PREPARED ACCORDING TO EXAMPLE 1 WITH COMPARISONS

| | Wavelength (mm) | Pure PMMA Lens Material (1) | UV Absorbing Lens Material Prepared According to Example 1 (2) | Human Lens (22 yrs) (3) | Human Lens (53 yrs) (4) |
|---|---|---|---|---|---|
| ↑ | 320 | 88% | <1.0% | <1.0% | <1.0% |
| ↑ | 330 | 89% | <1.0% | <1.0% | <1.0% |
| ↑ | 340 | 89% | <1.0% | <1.0% | <1.0% |
| ↑ | 350 | 90% | <1.0% | <1.0% | <1.0% |
| ↑ | 360 | 91% | <1.0% | <1.0% | <1.0% |
| UV-A  ↑ | 370 | 91% | <1.0% | <1.0% | <1.0% |
| ↓ | 380 | 91% | <1.0% | <1.0% | <1.0% |
| ↓ | 390 | 92% | 1.5% | 5.0% | <1.0% |
| ↓ | 395 | 92% | 6.0% | 10.0% | 2.0% |
| ↓ | 400 | 92% | 18.0% | 15.0% | 5.0% |
| ↑ | 450 | 92% | 88.0% | 85.0% | * |
| ↑ | 500 | 92% | 92.0% | 93.0% | * |
| ↑ | 550 | 92% | 92.0% | 95.0% | * |
| Visual | 600 | 92% | 92.0% | 95.0% | * |
| ↓ | 650 | 92% | 92.0% | 95.0% | * |
| ↓ | 700 | 92% | 92.0% | 95.0% | * |

(1) Direct transmittance of PMMA sample 1.05 mm thick.
(2) Direct transmittance of UV absorbing lens material .92 mm thick prepared according to the Example.
(3) Direct transmittance of human lens 22 years.
(4) Direct transmittance of human lens 53 years up to 400 nm; data not available over 400 nm.

As can be seen from Table 28, the UV absorbing lens material prepared in accordance with Example 1 has a capability to absorb ultraviolet radiation that is similar to the ultraviolet absorbing capability of a natural human lens.

In another embodiment of practice of this invention, a homopolymer of such a polymerizable chromophoric compound described above can also be formed, comminuted, and mixed with methyl methacrylate monomer, which is then polymerized to form the ultraviolet radiation absorbing lens of this invention. The molecular weight of the homopolymer must be sufficiently high to inhibit leaching. Leaching can also be inhibited or prevented by addition of cross-linking agents such as ethylene glycol dimethacrylate to the methyl methacrylate monomer/homopolymer mixture.

Although this invention has been described in detail with particular attention to certain preferred embodiments thereof, it will be understood that variations and modifications can be effected within the spirit and scope of the invention. The scope of the invention is defined in the following claims.

What is claimed is:

1. A method for forming an intraocular lens comprising the steps of:
   (a) co-polymerizing by solution polymerization a polymerizable derivative of dihydroxybenzophenone and methyl methacrylate monomer to form a solid ultraviolet radiation absorbing co-polymer additive;
   (b) dissolving the ultraviolet radiation absorbing co-polymer additive in methyl methacrylate monomer to thereby form a prepolymer solution;
   (c) curing the prepolymer solution in a mold to thereby form an intraocular lens comprising the ultraviolet radiation absorbing co-polymer additive physically trapped within a polymethylmethacrylate polymer matrix.

2. The method according to claim 1 wherein the polymerizable derivative of dihydroxybenzophenone comprises 2-hydroxy-4-(2-hydroxy-3-methacrylyloxy)-propoxybenzophenone.

3. The method according to claim 1 wherein the polymerizable derivative of dihydroxybenzophenone is monofunctional.

4. A method for forming an intraocular lens comprising the steps of:

(a) co-polymerizing a monofunctional polymerizable derivative of dihydroxybenzophenone and methyl methacrylate monomer to form a solid ultraviolet radiation absorbing co-polymer additive;

(b) dissolving the ultraviolet radiation absorbing co-polymer additive in methyl methacrylate monomer to thereby form a prepolymer solution;

(c) curing the prepolymer solution in a mold to thereby form an intraocular lens comprising the ultraviolet radiation absorbing co-polymer additive physically trapped within a polymethylmethacrylate polymer matrix.

5. The method according to claim 4 wherein the polymerizable derivative of dihydroxybenzophenone comprises 2-hydroxy-4-(2-hydroxy-3-methacrylyloxy)-propoxybenzophenone.

6. An intraocular lens for implantation into the human eye comprising an ultraviolet radiation absorbing co-polymer physically trapped within a polymethylmethacrylate polymer matrix, said lens being formed by the steps of:

(a) co-polymerizing by solution polymerization a polymerizable derivative of dihydroxybenzophenone with methyl methacrylate monomer to thereby form an ultraviolet radiation absorbing co-polymer additive;

(b) dissolving the ultraviolet radiation absorbing co-polymer additive in methyl methacrylate monomer to thereby form a prepolymer solution;

(c) curing the prepolymer solution in a mold to thereby form an intraocular lens comprising the ultraviolet radiation absorbing co-polymer additive physically trapped within a polymethylmethacrylate polymer matrix.

7. An intraocular lens for implantation into the human eye according to claim 6 wherein the polymerizable derivative of dihydroxybenzophenone comprises 2-hydroxy-4-(2-hydroxy-3-methacrylyloxy)propoxybenzophenone.

8. An intraocular lens for implantation into the human eye according to claim 6 wherein the polymerizable derivative of dihydroxybenzophenone is monofunctional.

9. An intraocular lens for implantation into the human eye comprising an ultraviolet radiation absorbing co-polymer physically trapped within a polymethylmethacrylate polymer matrix, said lens being formed by the steps of:

(a) co-polymerizing a monofunctional polymerizable derivative of dihydroxybenzophenone with methyl methacrylate monomer to thereby form an ultraviolet radiation absorbing co-polymer additive;

(b) dissolving the ultraviolet radiation absorbing co-polymer additive in methyl methacrylate monomer to thereby form a prepolymer solution;

(c) curing the prepolymer solution in a mold to thereby form an intraocular lens comprising the ultraviolet radiation absorbing co-polymer additive physically trapped within a polymethylmethacrylate polymer matrix.

10. An intraocular lens for implantation into the human eye according to claim 9 wherein the polymerizable derivative of dihydroxybenzophenone comprises 2-hydroxy-4-(2-hydroxy-3-methacrylyloxy)propoxybenzophenone.

* * * * *